United States Patent
Holland-Staley

(12) 
(10) Patent No.: US 8,173,795 B2
(45) Date of Patent: May 8, 2012

(54) METHODS AND COMPOSITIONS FOR IDENTIFYING AND CHARACTERIZING HEPATITIS C

(75) Inventor: Carol Holland-Staley, Troy, MI (US)

(73) Assignee: Lab 21 Limited, Cambridge (GB)

( * ) Notice: Subject to any disclaimer, the term of this patent is extended or adjusted under 35 U.S.C. 154(b) by 382 days.

(21) Appl. No.: 12/176,577

(22) Filed: Jul. 21, 2008

(65) Prior Publication Data

US 2009/0047663 A1    Feb. 19, 2009

Related U.S. Application Data

(60) Division of application No. 10/938,405, filed on Sep. 9, 2004, now abandoned, which is a continuation of application No. PCT/US03/07585, filed on Mar. 11, 2003.

(60) Provisional application No. 60/363,603, filed on Mar. 11, 2002.

(51) Int. Cl.
  *C07H 21/04* (2006.01)
  *C12Q 1/68* (2006.01)

(52) U.S. Cl. .................... 536/24.3; 435/6.12

(58) Field of Classification Search .............. 536/22.1, 536/24.33; 435/6
  See application file for complete search history.

(56) References Cited

U.S. PATENT DOCUMENTS

| | | | |
|---|---|---|---|
| 5,372,928 A | 12/1994 | Miyamura et al. | |
| 5,571,673 A | 11/1996 | Picone | |
| 6,127,116 A | 10/2000 | Rice et al. | |
| 6,150,087 A * | 11/2000 | Chien | 435/5 |
| 6,153,421 A * | 11/2000 | Yanagi et al. | 435/235.1 |
| 6,242,187 B1 | 6/2001 | Capon et al. | |
| 6,280,940 B1 | 8/2001 | Potts et al. | |
| 6,680,059 B2 * | 1/2004 | Sallberg et al. | 424/225.1 |
| 7,201,911 B1 * | 4/2007 | Yanagi et al. | 424/218.1 |
| 7,338,759 B1 * | 3/2008 | Rice et al. | 435/6 |
| 2003/0125270 A1 * | 7/2003 | Blatt et al. | 514/44 |

FOREIGN PATENT DOCUMENTS

| | | |
|---|---|---|
| EP | 0435229 | 7/1991 |
| WO | WO-94/25601 | 11/1994 |
| WO | WO-94/25602 | 11/1994 |
| WO | WO-99/06597 | 2/1999 |
| WO | WO-01/79540 | 10/2001 |
| WO | WO-02/08447 | 1/2002 |
| WO | WO-03/077729 | 9/2003 |

OTHER PUBLICATIONS

Lowe et al., A computer program for selection of oligonucleotide primers for polymerase chain reactions. Nucleic Acids Research, vol. 18, No. 7, pp. 1757-1761, 1990.*

Livache, T. et al., "Detection of HIV1 DNA in biological samples by an homogeneous assay: fluoescence measurement of double stranded RNA synthesized from amplified DNA," Analytical Biochemistry, 217:248-254 (1994).

Roggendorf, M. et al., "Rational use of diagnostic tools in hepatitis C," J. of Hepatology, 24(2):26-34 (1996).

Berger, A. et al., "Quantification of viral load: clinical relevance for human immunodeficiency virus, hepatitis B virus and hepatitis C virus infection," Intervirology, 41:24-34 (1998).

* cited by examiner

*Primary Examiner* — Prabha Chunduru

(74) *Attorney, Agent, or Firm* — Gilberto M. Villacorta; Sunit Talapatra; Foley & Lardner LLP

(57) ABSTRACT

The invention provides novel methods and compositions for amplifying portions of the HCV genome. The nucleic acid sequences set forth as SEQ ID NOS:1-64 derived from HCV cDNA and functional equivalents thereof, kits containing same, and methods employing same, are useful for the identification and characterization of HCV in biological samples.

11 Claims, 2 Drawing Sheets

SEQUENCE LISTING

<160> NUMBER OF SEQ ID NOS: 64

<210> SEQ ID NO 1
<211> LENGTH: 17
<212> TYPE: DNA
<213> ORGANISM: Artificial Sequence
<220> FEATURE:
<223> OTHER INFORMATION: Primer

<400> SEQUENCE: 1
cctgcttgtg gatgatg                                                  17

<210> SEQ ID NO 2
<211> LENGTH: 29
<212> TYPE: DNA
<213> ORGANISM: Artificial Sequence
<220> FEATURE:
<223> OTHER INFORMATION: Primer

<400> SEQUENCE: 2
ctgatgaaat tccacatgtg cttcgccca                                     29

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
ctactcctgc tcctgctggc gtt                                           23

<210> SEQ ID NO 4
<211> LENGTH: 32
<212> TYPE: DNA
<213> ORGANISM: Artificial Sequence
<220> FEATURE:
<223> OTHER INFORMATION: Primer

<400> SEQUENCE: 4
cactcttcca tctcatcgaa ctcctggtag ag                                 32

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
gtgtgggtyc ccccctcaa c                                              21

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
gccgacatgc atgycatgat gtattt                                        26

```
<210> SEQ ID NO 7
<211> LENGTH: 17
<212> TYPE: DNA
<213> ORGANISM: Artificial Sequence
<220> FEATURE:
<223> OTHER INFORMATION: Primer

<400> SEQUENCE: 7
gagcccgtcg tcttctc                                              17

<210> SEQ ID NO 8
<211> LENGTH: 17
<212> TYPE: DNA
<213> ORGANISM: Artificial Sequence
<220> FEATURE:
<223> OTHER INFORMATION: Primer

<400> SEQUENCE: 8
ggccgggaca asaacca                                              17

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
tcggaccttt acttggtcac gag                                       23

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
aggaacttgc cwtaggtgga gta                                       23

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
cgccggcgca ccggaatgac atc                                       23

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
tactccacct atggcaagtt cct                                       23

<210> SEQ ID NO 13
<211> LENGTH: 25
<212> TYPE: DNA
<213> ORGANISM: Artificial Sequence
<220> FEATURE:
<223> OTHER INFORMATION: Primer
```

<400> SEQUENCE: 13
gagtgctatg acgcgggctg tgctt          25

<210> SEQ ID NO 14
<211> LENGTH: 17
<212> TYPE: DNA
<213> ORGANISM: Artificial Sequence
<220> FEATURE:
<223> OTHER INFORMATION: Primer

<400> SEQUENCE: 14
gagtggcact catcaca          17

<210> SEQ ID NO 15
<211> LENGTH: 17
<212> TYPE: DNA
<213> ORGANISM: Artificial Sequence
<220> FEATURE:
<223> OTHER INFORMATION: Primer

<400> SEQUENCE: 15
catctcatyt tctgcca          17

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tcgactgtct grgtgacaca          20

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
ccatcgtggg aycaaatgtg gaagtgt          27

<210> SEQ ID NO 18
<211> LENGTH: 26
<212> TYPE: DNA
<213> ORGANISM: Artificial Sequence
<220> FEATURE:
<223> OTHER INFORMATION: Primer

<400> SEQUENCE: 18
aaatacatca tgrcatgcat gtcggc          26

<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
tgggcgaagc acatgtggaa tttcatcag          29

```
<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
gccatcctct ctcctggtgc cct                                              23

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
cacccayccc cccaakatgt t                                                21

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
ccggrggtca ttaygtscaa atgg                                             24

<210> SEQ ID NO 23
<211> LENGTH: 18
<212> TYPE: DNA
<213> ORGANISM: Artificial Sequence
<220> FEATURE:
<223> OTHER INFORMATION: Primer

<400> SEQUENCE: 23
cgcggggttt ccaggcag                                                    18

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ggcacytaca tctatgayca                                                  20

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
tcatcttcag tccgatggag a                                                21

<210> SEQ ID NO 26
<211> LENGTH: 23
<212> TYPE: DNA
<213> ORGANISM: Artificial Sequence
<220> FEATURE:
<223> OTHER INFORMATION: Primer
```

```
<400> SEQUENCE: 26
atgccgctra tgaarttcca cat                                           23

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
ctgaaygcca tcatggargc ca                                            22

<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
ccaatggaga agaaggtca                                                19

<210> SEQ ID NO 29
<211> LENGTH: 18
<212> TYPE: DNA
<213> ORGANISM: Artificial Sequence
<220> FEATURE:
<223> OTHER INFORMATION: Primer

<400> SEQUENCE: 29
atgtggagac atcctgca                                                 18

<210> SEQ ID NO 30
<211> LENGTH: 18
<212> TYPE: DNA
<213> ORGANISM: Artificial Sequence
<220> FEATURE:
<223> OTHER INFORMATION: Primer

<400> SEQUENCE: 30
ttgtggcctg ttgtagga                                                 18

<210> SEQ ID NO 31
<211> LENGTH: 18
<212> TYPE: DNA
<213> ORGANISM: Artificial Sequence
<220> FEATURE:
<223> OTHER INFORMATION: Primer

<400> SEQUENCE: 31
gcgcattctt ccatctca                                                 18

<210> SEQ ID NO 32
<211> LENGTH: 18
<212> TYPE: DNA
<213> ORGANISM: Artificial Sequence
<220> FEATURE:
<223> OTHER INFORMATION: Primer

<400> SEQUENCE: 32
ccgaaacgct gaygtcat                                                 18
```

```
<210> SEQ ID NO 33
<211> LENGTH: 18
<212> TYPE: DNA
<213> ORGANISM: Artificial Sequence
<220> FEATURE:
<223> OTHER INFORMATION: Primer

<400> SEQUENCE: 33
ggatggaggc tgctcagc                                                 18

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
agacccgacc tttaccat                                                 18

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ttacccgtgt gtcaagacca                                               20

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36
ccaatgatgg aratgcag                                                 18

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
cctttgcsct agcgcata                                                 18

<210> SEQ ID NO 38
<211> LENGTH: 18
<212> TYPE: DNA
<213> ORGANISM: Artificial Sequence
<220> FEATURE:
<223> OTHER INFORMATION: Primer

<400> SEQUENCE: 38
gagcactacg ctgtcgaa                                                 18

<210> SEQ ID NO 39
<211> LENGTH: 18
<212> TYPE: DNA
<213> ORGANISM: Artificial Sequence
<220> FEATURE:
<223> OTHER INFORMATION: Primer
```

```
<400> SEQUENCE: 39
tggctgtggc tagaacca                                                  18

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
gtaggcccca aaaccaag                                                  18

<210> SEQ ID NO 41
<211> LENGTH: 18
<212> TYPE: DNA
<213> ORGANISM: Artificial Sequence
<220> FEATURE:
<223> OTHER INFORMATION: Primer

<400> SEQUENCE: 41
gcyctgaaca agcccacg                                                  18

<210> SEQ ID NO 42
<211> LENGTH: 18
<212> TYPE: DNA
<213> ORGANISM: Artificial Sequence
<220> FEATURE:
<223> OTHER INFORMATION: Primer

<400> SEQUENCE: 42
acatctgrgt gactggtc                                                  18

<210> SEQ ID NO 43
<211> LENGTH: 19
<212> TYPE: DNA
<213> ORGANISM: Artificial Sequence
<220> FEATURE:
<223> OTHER INFORMATION: Primer

<400> SEQUENCE: 43
ccygtaatat ttagtccca                                                 19

<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44
tggaaatcaa ggtcatca                                                  18

<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45
gtagctacta tgggctcaa                                                 19
```

```
<210> SEQ ID NO 46
<211> LENGTH: 18
<212> TYPE: DNA
<213> ORGANISM: Artificial Sequence
<220> FEATURE:
<223> OTHER INFORMATION: Primer

<400> SEQUENCE: 46
gcttgctcga tgtacggg                                                    18

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47
cccgtcatct ttagtccta                                                   19

<210> SEQ ID NO 48
<211> LENGTH: 18
<212> TYPE: DNA
<213> ORGANISM: Artificial Sequence
<220> FEATURE:
<223> OTHER INFORMATION: Primer

<400> SEQUENCE: 48
tggagattaa ggttatca                                                    18

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
gattgcacta tgggtcgaa                                                   19

<210> SEQ ID NO 50
<211> LENGTH: 18
<212> TYPE: DNA
<213> ORGANISM: Artificial Sequence
<220> FEATURE:
<223> OTHER INFORMATION: Primer

<400> SEQUENCE: 50
gcttgctcga tgtaagga                                                    18

<210> SEQ ID NO 51
<211> LENGTH: 17
<212> TYPE: DNA
<213> ORGANISM: Artificial Sequence
<220> FEATURE:
<223> OTHER INFORMATION: Primer

<400> SEQUENCE: 51
ggccgggaca asaacca                                                     17

<210> SEQ ID NO 52
<211> LENGTH: 23
<212> TYPE: DNA
<213> ORGANISM: Artificial Sequence
<220> FEATURE:
<223> OTHER INFORMATION: Primer
```

<400> SEQUENCE: 52
tcggaccttt acttggtcac gag                                               23

<210> SEQ ID NO 53
<211> LENGTH: 23
<212> TYPE: DNA
<213> ORGANISM: Artificial Sequence
<220> FEATURE:
<223> OTHER INFORMATION: Primer

<400> SEQUENCE: 53
cgccggcgca ccggaatgac atc                                               23

<210> SEQ ID NO 54
<211> LENGTH: 23
<212> TYPE: DNA
<213> ORGANISM: Artificial Sequence
<220> FEATURE:
<223> OTHER INFORMATION: Primer

<400> SEQUENCE: 54
tactccacct atggcaagtt cct                                               23

<210> SEQ ID NO 55
<211> LENGTH: 23
<212> TYPE: DNA
<213> ORGANISM: Artificial Sequence
<220> FEATURE:
<223> OTHER INFORMATION: Primer

<400> SEQUENCE: 55
aggaacttgc cwtaggtgga gta                                               23

<210> SEQ ID NO 56
<211> LENGTH: 17
<212> TYPE: DNA
<213> ORGANISM: Artificial Sequence
<220> FEATURE:
<223> OTHER INFORMATION: Primer

<400> SEQUENCE: 56
gagtggcact catcaca                                                      17

<210> SEQ ID NO 57
<211> LENGTH: 17
<212> TYPE: DNA
<213> ORGANISM: Artificial Sequence
<220> FEATURE:
<223> OTHER INFORMATION: Primer

<400> SEQUENCE: 57
catctcatyt tctgcca                                                      17

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
tcgactgtct grgtgacaca                                                   20

```
<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
gagtgctatg acgcgggctg tgctt                                  25

<210> SEQ ID NO 60
<211> LENGTH: 27
<212> TYPE: DNA
<213> ORGANISM: Artificial Sequence
<220> FEATURE:
<223> OTHER INFORMATION: Primer

<400> SEQUENCE: 60
ccatcgtggg aycaaatgtg gaagtgt                                27

<210> SEQ ID NO 61
<211> LENGTH: 26
<212> TYPE: DNA
<213> ORGANISM: Artificial Sequence
<220> FEATURE:
<223> OTHER INFORMATION: Primer

<400> SEQUENCE: 61
aaatacatca tgrcatgcat gtcggc                                 26

<210> SEQ ID NO 62
<211> LENGTH: 26
<212> TYPE: DNA
<213> ORGANISM: Artificial Sequence
<220> FEATURE:
<223> OTHER INFORMATION: Primer

<400> SEQUENCE: 62
gccgacatgc atgycatgat gtattt                                 26

<210> SEQ ID NO 63
<211> LENGTH: 32
<212> TYPE: DNA
<213> ORGANISM: Artificial Sequence
<220> FEATURE:
<223> OTHER INFORMATION: Primer

<400> SEQUENCE: 63
cactcttcca tctcatcgaa ctcctggtag ag                          32

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
gtgtgggttc ccccctcaa cgt                                     23
```

METHODS AND COMPOSITIONS FOR IDENTIFYING AND CHARACTERIZING HEPATITIS C

RELATED APPLICATIONS

The present application is a divisional of U.S. application Ser. No. 10/938,405 filed on Sep. 9, 2004 now abandoned which is a continuation of PCT Application No. PCT/US03/07585 filed on Mar. 11, 2003 which claims priority to U.S. Provisional Application Ser. No. 60/363,603 filed on Mar. 11, 2002, which are all herein incorporated by reference.

BACKGROUND OF THE INVENTION

The Hepatitis C virus (HCV) is the major etiologic agent for non-A, non-B hepatitis. It is estimated that around 400 million people or >2% of the world's population are infected (Di Bisceglie, A. M. (1998) Hepatitis C. Lancet 351:351-5; Houghton M. (1996), p. 1035-1058. In B. N. Fields and D. M. Knipe and H. P. M. (ed.), Fields' Virology, 3rd ed. Lippincott-Raven, Philadelphia/New York). HCV usually results in a chronic infection in 60 to 80% of infected individuals with 20% having progression to cirrhosis, hepatocellular carcinoma or chronic liver failure. At least 6 major viral genotypes and over 50 proposed subtypes of HCV have been identified worldwide (Simmonds, P. et al. (1994) Identification of genotypes of hepatitis C virus by sequence comparisons in the core, E1 and NS-5 regions. *J Gen Virol* 75:1053-1061). These genotypes are based on nucleotide and amino acid sequence diversity with the most divergent isolates differing by more than 30% (Bréchot, C. (1996) Hepatitis C virus: Molecular biology and genetic variability. *Digestive Diseases and Sciences* 41:6S-21S; Bukh, J. et al. (1995) Genetic heterogeneity of hepatitis C virus: quasispecies and genotypes. *Semin Liver Dis* 15:41-63). Among the different types, there are regions which are highly conserved and have sequence homology close to 100%, however, in highly variable regions such as the envelope proteins homology is <70% (Booth, J. C. et al. (1998) Comparison of the rate of sequence variation in the hypervariable region of E2/NS1 region of hepatitis C virus in normal and hypogammaglobulinemic patients. *Hepatology* 27:223-27; Hayashi, N. et al. (1993) Molecular cloning and heterogeneity of the human hepatitis C virus (HCV) genome. *J Hepatol* 17:S94-107; Hijikata, M. et al. (1991) Hypervariable regions in the putative glycoprotein of hepatitis C virus. *Biochem Biophys Res Commun* 175:220-228; Kato, N. et al. (1992) Marked sequence diversity in the putative envelope proteins of hepatitis C viruses. *Virus Res* 22:107-123; Lesniewski, R. R. et al. (1993) Hypervariable 5'-terminus of hepatitis C virus E2/NS1 encodes antigenically distinct variants. *J Med Virol* 40:150-156; Pozzetto, B. et al. (1996) Structure, genomic organization, replication and variability of hepatitis C virus. *Nephrol Dial Transplant* 11 [Suppl 4]:2-5; Vizmanos, J. L. et al. (1998) Degree and distribution of variability in the 5' untranslated, E1, E2/NS1 and NS5 regions of the hepatitis C virus (HCV). *J Viral Hepat* 5:227-240).

HCV is a member of the Flaviviridae family whose other members include the Flaviviruses and Pestiviruses (Kato, N. et al. (1991) Molecular structure of the Japanese hepatitis C viral genome. *FEBS Lett* 280:325-328). The HCV genome is a positive-stranded RNA of ~9.5 kb which contains a single open reading frame encoding a polyprotein of 3010 to 3033 amino acids (Takamizawa, A. et al. (1991) Structure and organization of the hepatitis C virus genome isolated from human carriers. *J Virol* 65:1105-1113). Proteolytic processing of the polyprotein is accomplished by host and viral proteases. Host signal peptidases cleave the structural proteins which are located in the 5' end, while two viral proteases cleave the non-structural proteins. These cleavages result in at least 10 viral proteins in the order $NH_2$—C-E1-E2-p7-NS2-NS3-NS4A-NS4B-NS5A-NS5B-COOH. There are also non-coding regions located at the 5' and 3' ends which are involved in ribosome binding and replication initiation, respectively.

One of the viral proteases, the NS3 protease, is encoded by the N-terminal region of the HCV NS3 gene. It consists of 181 amino acids and is a chymotrypsin-like serine-protease responsible for cleavage of the non-structural proteins of HCV (Bartenschlager, R. et al. (1993) Nonstructural protein 3 of the hepatitis C virus encodes a serine-type proteinase required for cleavage at the NS3/4 and NS4/5 junctions. *J Virol* 67:3835-3844; Eckart, M. R. et al. (1993) The hepatitis C virus encodes a serine protease involved in processing of the putative nonstructural proteins from the viral polyprotein precursor. *Biochem Biophys Res Commun* 192:399-406; Gallinari, P. et al. (1998) Multiple enzymatic activities associated with recombinant NS3 protein of hepatitis C virus. *J Virol* 72:6758-6769; Hahm, B. et al. (1995) NS3-4A of hepatitis C virus is a chymotrypsin-like protease. *J Virol* 69:2534-2539; Hijikata, M. et al. (1993) Two distinct proteinase activities required for the processing of a putative nonstructural precursor protein of hepatitis C virus. *J Virol* 67:4665-4675; Hijikata, M. et al. (1993) Proteolytic processing and membrane association of putative nonstructural proteins of hepatitis C virus. *Proc Natl Acad Sci USA.* 90:10773-10777; Manabe, S. et al. (1994) Production of nonstructural proteins of hepatitis C virus requires a putative viral protease encoded by NS3. *Virology* 198:636-644; Tomei, L. et al. (1993) NS3 is a serine protease required for processing of hepatitis C virus polyprotein. *J Virol* 67:4017-4026). Processing of the structural proteins by NS3 occurs in a well ordered cascade with the first cleavage occurring between NS3 and NS4A followed by NS5A-NS5B, NS4A-NS4B and NS4B-NS5A (Bartenschlager, R. et al. (1994) Kinetic and structural analysis of hepatitis C virus polyprotein processing. *J Virol* 68:5045-5055; D'Souza, E. D. et al. (1994) Analysis of NS3-mediated processing of the hepatitis C virus non-structural region in vitro. *J Gen Virol* 75:3469-3476; Eckart M. R., et al., 1993, supra; Failla, C. et al. (1994) Both NS3 and NS4A are required for proteolytic processing of hepatitis C virus non-structural proteins. *J Virol* 68:3753-3760; Kolykhalov, A. A. et al. (1994) Specificity of the hepatitis C virus NS3 serine protease: effects of substitutions at the 3/4A, 4A/4B, 4B/5A, and 5A/5B cleavage sites on polyprotein processing. *J Virol* 68:7525-7533; Shimotohno, K. et al. (1995) Processing of the hepatitis C virus precursor protein. *J Hepatol* 22:87-92; Shoji, I. et al. 1999 Internal processing of hepatitis C virus NS3 protein. *Virology* 254:315-323; Tomei, L. et al., 1993, supra). The cleavage between NS3 and NS4A occurs in cis, while the other cleavages are in trans. The virus-encoded cofactor, NS4A is necessary for efficient NS3 function. Proteolytic processing efficiency has been shown to increase dramatically in the presence of the NS4A protein (Failla, C. et al. (1995) An amino-terminal domain of the hepatitis C virus NS3 proteinase is essential for the interaction with NS4A. *J Virol* 69:1769-1777; Failla, 1994, supra; Gallinari, P. et al. 1999 Modulation of hepatitis C virus NS3 protease and helicase activities through the interaction with NS4A. *Biochemistry* 38:5620-5632; Lin, C. et al. (1995) A central region in the hepatitis C virus NS4A protein allows formation of an active NS3-NS4A serine proteinase complex in vivo and in vitro. *J Virol* 69:4373-4380; Satoh, S. et al. (1995) The N-terminal region of hepatitis C virus nonstructural protein 3 (NS3) is essential for stable complex formation with NS4A. *J*

Virol 69:4255-4260; Tanji, Y. et al. (1995) Hepatitis C virus-encoded nonstructural protein NS4A has versatile functions in viral protein processing. *J Virol* 69:1575-1581). In addition, NS3 contains a tetrahedrally bound zinc atom, which appears to play a structural role (De Francesco, R. et al. (1996) A zinc binding site in viral serine proteinases. *Biochemistry* 35:13282-13287; Stempniak, M. et al. (1997) The NS3 proteinase domain of hepatitis C virus is a zinc-containing enzyme. *J Virol* 71:2881-2886).

Recently, considerable progress has been made in determining how the NS3 protease processes the HCV polypeptide (Kolykhalov, A. A. et al., 1994 supra; Steinkühler, C. et al. (1996) Activity of purified hepatitis C virus protease NS3 on peptide substrates. *J Virol* 70:6694-6700; Urbani, A. et al. (1997) Substrate specificity of the hepatitis C virus serine protease NS3. *J Biol Chem* 272:9204-9209). Models for how the protease interacts with cofactors and the substrate have identified four domains, which are involved in enzyme function Barbato, G. et al. 1999. The solution structure of the N-terminal proteinase domain of the hepatitis C virus (HCV) NS3 protein provides new insights into its activation and catalytic mechanism. *J Mol Biol* 289:371-384). These are the catalytic triad, cofactor and metal binding sites and the substrate-binding pocket. These domains are well defined and contain amino acid residues that are highly conserved in all HCV protease genes sequenced to date (See FIG. 1 in Holland-Staley, C. A., et al. (2002) Genetic diversity and response to IFN of the NS3 protease gene from clinical strains of the hepatitis C virus. *Arch Virol* 147:1385-1406, which is incorporated herein by reference). Despite this recent burst of structural information and studies showing direct involvement and conservation of amino acid residues, the impact of natural sequence variability on enzyme function is not well understood. In addition, the effects of anti-viral therapy on the NS3 protease sequence are unknown. Elucidation of the natural genetic diversity of the HCV NS3 protease in patient samples is of significant medical as well as theoretical interest. Though all HCV NS3 proteases sequenced to date contain conserved active-site amino acids, sequence variation throughout the NS3 gene is significant (Martell, M. et al. (1992) Hepatitis C virus (HCV) circulates as a population of different but closely related genomes:quasispecies nature of HCV distribution. *J Virol.* 66:3225-32; Okamoto, H. et al. (1992) Genetic drift of hepatitis C virus during an 8.2-year infection in a chimpanzee: variability and stability. *Virology* 190:894-899; Okamoto, H. et al. (1992) supra). Also, the presence of multiple species within the same patient, known as quasispecies, creates a potential problem for drug development and resistance. Understanding the extent of NS3 sequence variation in clinical strains will allow more effective development of drugs targeting the HCV protease. For this, data must be available that describes sequence variability as it occurs in HCV-infected persons.

Helicases are enzymes that are responsible for unwinding DNA/DNA, RNA/DNA and RNA/RNA duplexes in a 3'-to-5' direction. (Bartenschlager, R. et al., 1993, supra; Hahm B., et al., 1995, supra; Tomei, et al., 1993, supra). In addition, helicase enzymes have been proposed to play roles in viral replication and recombination, viral control of host cellular functions, mRNA stability including splicing or processing, transcription, transport, and translation initiation of RNA (Lüking, et al. (1998) The protein family of RNA helicases. *Crit. Rev. Biochem. Mol. Biol.* 33:259-296). The HCV NS3 helicase/NTPase contains 450 amino acids. The NTPase component hydrolyzes nucleoside 5'-triphosphates, providing the energy requirements. The helicase/NTPase, along with the NS3 protease and NS5b RNA-dependent polymerase, are believed to make up a large complex, which is responsible for viral RNA replication. Recently, considerable progress has been made in determining the structure of the HCV NS3 helicase and its mechanism of duplex unwinding. At least three different crystal structures have been published (Paolini, Cho et al., 1998, supra; Kim et al., 1998, supra; and Yao et al. 1997, supra). In all three, the enzyme was shown to contain 3 domains, with domains 1 and 2 being structurally similar. The enzyme contains seven motifs, including two motifs which are involved in NTP-binding and hydrolysis (motif I [GxGKS] and motif II [DExH]) and one that is involved in ATP hydrolysis and RNA unwinding (motif VI). Most of the motifs are located between the structural domains 1 and 2, with domain 3 separated from the other two by the binding of the nucleotide. Investigators have identified highly conserved residues within each motif. These motifs, along with comparison analysis to other helicases, reveal it to be a member of the DEAD-box family of RNA helicases, specifically the DExH subfamily. Magnesium is required for both the helicase and NTPase activities.

The only FDA approved therapy for hepatitis C infection is interferon (IFN) or pegylated-interferon with or without ribaviron. Interferon production has been shown to be induced after infections with bacteria, parasites and viruses as well as in response to tumors. Interferons are secreted proteins in the cytokine family, which indirectly inhibit the viral life cycle by binding to cellular receptors, thus inducing protein synthesis (Hijikata, M. et al. (1993) Proteolytic processing and membrane association of putative nonstructural proteins of hepatitis C virus. *Proc Natl Acad Sci USA*. 90:10773-10777). Interferon inducible genes contain a promoter region, termed the IFN-stimulated response element (ISRE). Over 30 genes are induced by interferon, however, the function of most of these genes is unknown (Holmes, E. C. et al. (2000) The causes and consequences of genetic variation in dengue virus. *Trends Microbiol* 8:74-77).

Recently it has been suggested that a short stretch of 40 amino acids in the HCV NS5A gene play a role in IFN resistance, however, while this appears true for some Japanese isolates other investigators have conflicting data. The effects of interferon therapy on the other structural genes is unknown.

SUMMARY OF THE INVENTION

The present invention is based, at least in part, on the discovery of novel, isolated nucleic acid sequences for amplifying and sequencing portions of the HCV genome. The present invention provides novel sequences and methods of using same, which consistently amplify the HCV genome. The nucleic acid sequences of the present invention are useful as reagents for detecting and identifying viral sequences in biological samples and enable the further characterization of the HCV genome. The methods described herein, the nucleic acid sequences set forth as SEQ ID NOS:1-64 and functional equivalents thereof, as well as the kits containing them, are useful for accurately determining the presence of HCV in biological samples, as well as the specific sequence of a portion of the HCV genome. The nucleic acid sequences and methods of the present invention may be useful for: (i) detecting HCV infection, including early stage detection; (ii) identification of the type of HCV infection; (iii) detection of variant strains of HCV including heterogenicity in a patient; (iv) detection of a mutation in the HCV nucleic acid that is responsible for resistance or sensitivity to a therapy; (v) detection of new mutations in the HCV genome that are correlated with resistance or sensitivity to a drug therapy; (vi)

determining whether treatment with an agent, e.g., an anti-viral agent, will be effective; (vii) determining whether treatment with an agent, e.g., an anti-viral agent, should or should not be continued; (viii) identification of the interaction between HCV and other viruses and/or diseases; (ix) generating a nucleic acid, e.g., DNA, vaccine, which may be patient specific; and (x) development of new drugs, e.g., based on x-ray crystallography.

The present invention features novel, isolated primer sequences from the HCV genome set forth herein as SEQ ID NOS:1-64 (Tables 1A-G). Sequences which correspond to the HCV 1a and 1b subtypes are set forth as SEQ ID NOS:1-23 and SEQ ID NO:64 (Tables 1A and 1G); sequences which correspond to the HCV 2a subtype are set forth as SEQ ID NOS:24-27 (Table 1B); sequences which correspond to the HCV 2b subtype are set forth as SEQ ID NOS:28-42 (Table 1C); sequences which correspond to the HCV 3a subtype are set forth as SEQ ID NOS:43-46 (Table 1D); sequences which correspond to the HCV 3b subtype are set forth as SEQ ID NOS:47-50 (Table 1E); and sequences which correspond to the HCV 4a subtype are set forth as SEQ ID NOS:51-63 (Table 1F).

In one embodiment, the present invention features an oligonucleotide selected from the group consisting of SEQ ID NOS:1-64. In another embodiment, the oligonucleotides of the invention are at least 80%, 81%, 82%, 83%, 84%, 85%, 86%, 87%, 88%, 89%, 90%, 91%, 92%, 93%, 94%, 95%, 96%, 97%, 98%, 99% or more identical to the nucleotide sequences set forth in SEQ ID NOS:1-64. In yet another embodiment, the oligonucleotides of SEQ ID NOS:1-64 are at least 4, 8, 10, 11, 12, 13, 14, 15, 16, 17, 18, 19, 20, or more nucleotides in length. It will be appreciated that the 5' end may contain greater variability (e.g., nucleic acid substitutions), yet remain functional (e.g., able to anneal to the NS3 and NS4 portion of the HCV genome). In another embodiment, the invention provides a combination of one or more oligonucleotides of the present invention. In yet another embodiment, the invention provides a set of oligonucleotides, also referred to herein as "primers" and "nucleic acid primer sequences," selected from the group consisting of two or more of the oligonucleotides of the present invention. In still another embodiment, the invention provides oligonucleotides which are able to amplify a patient sample having a nucleotide sequence selected from the group consisting of SEQ ID NOS:1-64, or complement thereof. In one aspect of the invention, the oligonucleotides of the present invention comprise a label for detection. Such labels may be, e.g., radioactive labels which may be incorporated by known methods (e.g., nick translation or kinasing), radioactive isotopes, biotin, fluorescent groups, chemiluminescent groups (e.g., dioxetanes, particularly triggered dioxetanes), digoxigenin, enzymes, antibodies, luminescent agents, precipitating agents, dyes, combinations thereof, and the like. Another aspect of the invention comprises a vector comprising an oligonucleotide of the present invention.

In yet another embodiment, the invention provides an oligonucleotide for amplifying a nucleic acid sequence in a sample, wherein the sample contains a nucleotide sequence selected from the group consisting of SEQ ID NOS:1-64, or the complement thereof. In one aspect of the invention, the sample is from a patient infected with HCV.

In another embodiment, the invention provides a nucleic acid sequence, wherein the nucleic acid sequence is a promoter-primer comprising an oligonucleotide of the present invention, wherein a 5' portion of the sequence includes a promoter sequence.

The amplified HCV nucleic acid sequences generated from the methods set forth herein may be cloned into a host vector with an expression promoter and used as a DNA vaccine to amplify a patient's response to the HCV virus, thereby providing a patient-specific DNA vaccine to HCV. In another aspect of the invention, the clone may be used to generate RNA for use as an antisense vaccine.

It will be appreciated that a sample used in the methods of the present invention may be a biological sample, e.g., from a patient infected with HCV. Such samples may include, without limitation, blood, plasma, serum, spinal fluid, lymph fluid, the external sections of the skin, respiratory, intestinal, and genitourinary tracts, tears, saliva, milk, urine, blood cells, tumors, organs, genomic DNA, RNA, or cDNA in solution or bound to a substrate, and also samples of in vitro cell culture constituents including, but not limited to, conditioned medium resulting from the growth of cells in cell culture medium, putatively virally infected cells, recombinant cells, and cell components, e.g., chromosome(s), organelles, paraffin embedded tissue, or membranes isolated from a cell.

In one embodiment of the invention, the serine protease portion of the HCV NS3 gene is analyzed. This can be accomplished by amplifying and sequencing the serine protease portion of the gene with the compositions and methods of the present invention. When a primer pair is employed as sequencing primers, either or both of the members of the pair may be suitably labeled, e.g., radioactive labels which may be incorporated by known methods (e.g., nick translation or kinasing), radioactive isotopes, biotin, fluorescent groups, chemiluminescent groups (e.g., dioxetanes, particularly triggered dioxetanes), digoxigenin, enzymes, antibodies, luminescent agents, precipitating agents, dyes, combinations thereof, and the like.

In another embodiment of the invention, the helicase portion of the HCV NS3 gene is analyzed. This can be accomplished by amplifying and sequencing the helicase portion of the gene with the compositions and methods of the present invention. When a primer pair is employed as sequencing primers, either or both of the members of the pair may be suitably labeled, e.g., radioactive labels which may be incorporated by known methods (e.g., nick translation or kinasing), radioactive isotopes, biotin, fluorescent groups, chemiluminescent groups (e.g., dioxetanes, particularly triggered dioxetanes), digoxigenin, enzymes, antibodies, luminescent agents, precipitating agents, dyes, combinations thereof, and the like.

Primer combinations, for example, including at least one forward and one reverse primer, which together can be used for amplification and/or sequencing of a relevant portion of the HCV genome, e.g., the NS3 or NS4 gene, may be suitably packaged in a kit. Nested pairs of amplification and sequencing primers are preferred. In one embodiment, the invention provides a kit for the detection of HCV, comprising one or more oligonucleotide of the present invention. In another embodiment, the kit comprises a set of primers selected from the group consisting of the oligonucleotides of the present invention. The primers in such kits may be labeled or unlabeled. The kit may also include additional reagents such as reagents for performing a polymerase chain reaction (PCR), a reverse transcriptase for conversion of the HCV RNA to cDNA for amplification, DNA polymerases, dNTP and ddNTP feedstocks. The kit may also include instructions for use.

The present invention also features novel methods for amplifying a target nucleic acid, e.g., specific regions of the HCV genome of a patient, such as NS3 and NS4 genes of the HCV genome, using the oligonucleotides of the present invention. The novel methods of the present invention may be used for, for example: (i) detecting HCV infection, including early stage detection; (ii) identification of the type of HCV infection; (iii) detection of variant strains of HCV including heterogenicity in a singe patient; (iv) detection of a mutation in the HCV nucleic acid that is responsible for resistance or sensitivity to a therapy; (v) detection of new mutations in the HCV genome that are correlated with resistance or sensitivity to a therapy; (vi) determining whether treatment with an agent, e.g., an anti-viral agent, will be effective; (vii) determining whether treatment with an agent, e.g., an anti-viral agent, should or should not be continued; (viii) identification of the interaction between HCV and other viruses and/or diseases; (ix) generating a nucleic acid, e.g., DNA, vaccine, which may be patient specific; and (x) development of new drugs, e.g., based on x-ray crystallography. This analysis may be performed by direct sequencing, or using other techniques for characterization of sequence polymorphisms, including but not limited to, hybridization with sequence-specific oligonucleotide probes.

Accordingly, in one embodiment, the invention provides methods for amplifying a target nucleic acid, e.g., portions of the NS3 or NS4 gene, by combining a target nucleic acid under conditions which allow for an amplification reaction to occur with one or more nucleic acid primer sequences of the present invention and other necessary amplification agents such as a nucleic acid polymerase and a plurality of nucleotides. In one aspect of the present invention, the amplification of a target nucleic acid sequence results in an increased amount of the amplified target nucleic acid. In yet another aspect of the invention, the target nucleic acid sequence is from the HCV genome, e.g., the NS3 or NS4A gene. In other aspects of the invention, the target nucleic acid is the serine protease portion of the NS3 gene. In still other aspects of the invention, the target nucleic acid is the helicase portion of the NS3 gene. In another aspect of the invention, a nucleic acid polymerase is used and may be selected from the group consisting of reverse transcriptase and thermostable DNA polymerase. In other embodiments of the invention, the amplified HCV nucleic acid is sequenced. In yet another aspect of the invention, the sequence is evaluated for mutations.

In another embodiment of the present invention, a method for detecting and characterizing HCV nucleic acids in a sample is provided by contacting the sample with one or more nucleic acid primer sequences of the present invention under conditions such that the HCV nucleic acids can hybridize with the primers of the invention, reverse transcribing and amplifying the nucleic acids to obtain amplified HCV nucleic acids, and detecting the presence of the amplified HCV nucleic acids. The amplified HCV nucleic acids may be further characterized by, for example, sequencing the amplified nucleic acids. In one aspect of the invention, the detection of the presence of the amplified HCV nucleic acids comprises contacting the amplified HCV nucleic acids with a labeled oligonucleotide to obtain labeled HCV nucleic acids and identifying the labeled nucleic acids. In still other aspects of the invention, the amplification of the nucleic acids may be accomplished by nucleic acid sequence-based amplification (NASBA), Transcription Mediated Amplification (TMA), polymerase chain reaction (PCR), other target amplification methods, signal amplification methods or probe amplification methods such as Ligase chain reaction. In yet another aspect of the invention, the methods further comprise the step of sequencing the amplified HCV nucleic acids. In still another embodiment, the methods further comprise evaluating the sequence for mutations.

Once sequenced, mutations in the HCV genome may be identified by comparing the sequence with a known or a control sequence, e.g., a consensus sequence. Thus, the present invention provides compositions and methods for identifying particular mutations in the HCV genome. With the knowledge of a particular mutation in the HCV genome from a patient sample, appropriate therapy or combination therapy for the patient may be identified and administered. For example, the methods of the present invention may be used to determine a particular treatment regimen depending on the genotype of HCV that has infected the patient. In another embodiment, the invention provides compositions and methods for determining whether a patient is sensitive or resistant to an agent by obtaining a sample from a patient comprising DNA, performing amplification, e.g., PCR, on the DNA from the patient sample using a nucleic acid primer sequence of the present invention, and analyzing the amplified product, for example, by sequencing, to identify particular mutations. In still other aspects of the invention, the agent may be an antiviral agent, such as a protease inhibitor, an inhibitor of the serine protease portion of the NS3 gene, an inhibitor of the helicase portion of the NS3 gene, alpha-interferon, ribavirin, pegylated interferon, or a combination thereof.

Because the primer sequences of the present invention were derived from conserved regions of the HCV genome, the compositions and methods described herein will aid in the detection and/or identification of variant strains of HCV. This, in turn, will lead to the development of additional immunological agents for the detection and diagnosis of HCV, as well as the development of additional polynucleotide agents for the detection and or treatment of HCV.

In yet another embodiment, the invention provides a method for determining whether an agent can or can not be used to treat an HCV patient by obtaining a sample from a patient infected with HCV, amplifying the patient sample using the nucleic acid primer sequences of the present invention, sequencing the resulting amplified HCV nucleic acid sequences, and identifying mutations in the amplified HCV nucleic acid sequence that correlate with resistance or sensitivity to an agent, thereby determining whether the agent can or can not be used to treat an HCV patient. In one aspect of the invention, the nucleic acid sequences are a set of primers.

In another embodiment, the invention provides a method for determining whether treatment with an agent should be continued in a patient infected with HCV, the method comprising obtaining two or more samples comprising DNA from a patient during the course of treatment, amplifying and sequencing a target nucleic acid sequence from the sample using the nucleic acid primer sequences of the present invention in the methods described herein, identifying mutations present in the amplified nucleic acid sequence that correlate with resistance or sensitivity to an agent, and continuing treatment when the mutations identified in the amplified product do not change during the course of treatment.

In still another embodiment, the invention provides a method for determining whether treatment with an agent should not be continued in a patient infected with HCV, the method comprising obtaining two or more samples comprising DNA from a patient during the course of treatment, amplifying and sequencing the target nucleic acid sequences from the samples using the nucleic acid primer sequences of the present invention in the methods described herein, identifying mutations present in the amplified nucleic acid sequence that correlate with resistance or sensitivity to an agent, and discontinuing treatment when the mutations identified in the amplified product change, e.g., an increase in the number of mutations during the course of treatment is an indicator of resistance to an agent.

The Specific Examples set forth below also establish a correlation between HCV type, particularly as determined by analysis of the NS3 gene, and the likelihood that the virus will be responsive to anti-viral therapy, e.g., alpha-IFN therapy. Thus, a further aspect of the invention is a method for evaluating a patient diagnosed as or suspected of having an HCV infection to assess whether therapy, e.g., alpha-IFN therapy, is likely to be successful, comprising the steps of obtaining a sample from the patient containing DNA, comparing the serine protease portion of the NS3 gene and/or the helicase portion of the NS3 gene, to consensus subtype sequences, wherein the presence of one or more mutations is indicative of resistance to the therapy. It will be appreciated that this same methodology may be used to determine whether the virus (and thus the patient), will be sensitive or resistant to other anti-viral agents such as a protease inhibitor, an inhibitor of the serine protease portion of the NS3 gene, and an inhibitor of the helicase portion of the NS3 gene.

In another embodiment, the invention features a method of assessing the efficacy of an agent for treating HCV, the method comprising comparing nucleic acid sequences in a first sample obtained from a patient exposed to an agent, wherein the nucleic acid sequences are amplified products from one or more nucleic acid primer sequences of the present invention, and nucleic acid sequences in a second sample obtained from a patient who has not been exposed to an agent, wherein the nucleic acid sequences are amplified products from one or more nucleic acid primer sequences of the present invention, wherein an increased number of mutations in the nucleic acid sequences from the first sample, relative to the second sample, is an indication that the agent is not efficacious in treating HCV.

The practice of the present invention will employ, unless otherwise indicated, conventional techniques of chemistry, molecular biology, microbiology, recombinant DNA, and immunology, which are within the skill of the art. Such techniques are explained fully in the literature. (See e.g., Maniatis, Fitsch & Sambrook, Molecular Cloning; A Laboratory Manual (1982); DNA Cloning, Volumes I and II (D. N Glover ed. 1985); Oligonucleotide Synthesis (M. J. Gait ed, 1984); Nucleic Acid Hybridization (B. D. Hames & S. J. Higgins eds. 1984); the series, Methods in Enzymology (Academic Press, Inc.), particularly Vol. 154 and Vol. 155 (Wu and Grossman, and Wu, eds., respectively)). All patents, patent applications, and publications mentioned herein, both supra and infra, are hereby incorporated herein by reference.

BRIEF DESCRIPTION OF THE DRAWINGS

FIG. 2A depicts a consensus tree of the parsimony analysis, while FIG. 2B depicts a bootstrap tree from the Neighbor-joining analysis.

DETAILED DESCRIPTION OF THE INVENTION

Figure 1:
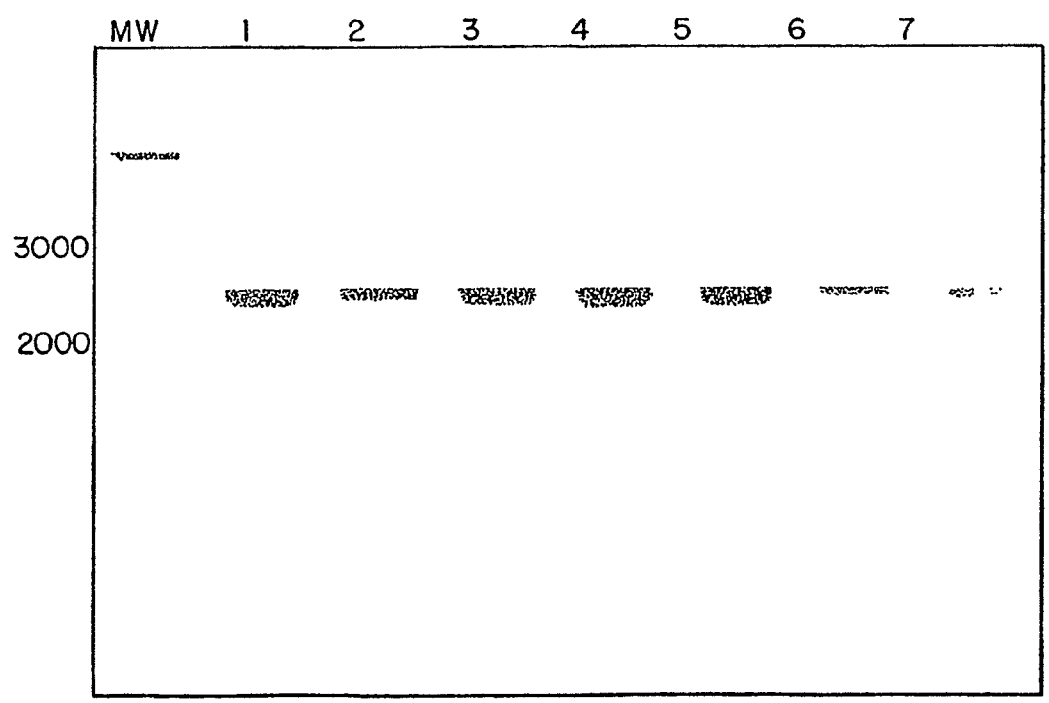
FIG. 1 depicts the results of a nested PCR reaction of Hepatitis C virus NS3 protease from 7 patient samples. The NS3 product is 2746 bp. The DNA MW ladder is in lane 1.

The term "agent" includes any known substance intended to treat an infection or disease, in particular, agents known to treat viral infections. The term "agent" is further intended to cover anti-viral agents including, but not limited to, a protease inhibitor, an inhibitor of the serine protease portion of the NS3 gene, an inhibitor of the helicase portion of the NS3 gene, alpha-interferon, ribavirin, and pegylated interferon.

The terms "amplification" or "amplify" include the reactions necessary to increase the number of copies of a nucleic acid sequence (e.g., a DNA sequence). For the purposes of this invention, amplification refers to the in vitro exponential increase in copy number of a target nucleic acid sequence, such as that mediated by a polymerase amplification reaction such as e.g., PCR, however, other amplification reactions encompassed by the invention include, e.g., RT-PCR (see, e.g., U.S. Pat. No. 4,683,202; Mullis et al.), and the ligase chain reaction (Barany, Proc. Natl. Acad. Sci. USA 88:189-193 (1991)).

The terms "Hepatitis C Virus" and "HCV" refer to the viral species that is the major etiological agent of BB-NANBH, the prototype isolate of which is identified in WO89/046699; EPO publication 318,216; and. U.S. Pat. No. 5,350,671, the disclosures of which are incorporated herein by reference. "HCV" as used herein includes the pathogenic strains capable of causing hepatitis C, and attenuated strains or defective interfering particles derived therefrom. The HCV genome is comprised of RNA. It is known that RNA-containing viruses have relatively high rates of spontaneous mutation, reportedly on the order of $10.\text{sup.}-3$ to $10.\text{sup.}-4$ per incorporated nucleotide (Fields & Knipe, "Fundamental Virology" (1986, Raven Press, N.Y.)). As heterogeneity and fluidity of genotype are inherent characteristics of RNA viruses, there will be multiple strains/isolates, which may be virulent or avirulent, within the HCV species.

The terms "hybridize" or "hybridization" are art-known and include the hydrogen bonding of complementary DNA and/or RNA sequences to form a duplex molecule.

The term "kit" is any manufacture (e.g., a package or container) comprising at least one reagent, e.g., a primer, for specifically amplifying and/or sequencing a portion of the HCV genome, the manufacture being promoted, distributed, or sold as a unit for performing the methods of the present invention. A kit may also include instructions for use.

The term "label" refers to a molecular moiety capable of detection including, by way of example, without limitation, radioactive labels which may be incorporated by known methods (e.g., nick translation or kinasing), radioactive isotopes, biotin, fluorescent groups, chemiluminescent groups (e.g., dioxetanes, particularly triggered dioxetanes), digoxigenin, enzymes, antibodies, luminescent agents, precipitating agents, dyes, and the like.

The term "nucleotides" refers to any nucleotide (including modified nucleotides, e.g., methylated or biotinylated nucleotides) that can be incorporated into a nucleic acid by a polymerase.

As used herein the term "nucleic acid" includes DNA molecules (e.g., cDNA or genomic DNA), RNA molecules (e.g., mRNA), and analogs of the DNA or RNA generated using nucleotide analogs or using nucleic acid chemistry. Typical modifications include methylation, biotinylation, and other art-known modifications. In addition, the nucleic acid molecule can be single-stranded or double-stranded.

The term "target nucleic acid" or "template" includes any nucleic acid intended to be copied in, e.g., a polymerase amplification reaction such as PCR.

The term "probe" refers to a structure comprised of a polynucleotide that forms a hybrid structure with a target sequence, due to complementarity of at least one sequence in the probe with a sequence in the target region. The polynucleotide regions of probes may be composed of DNA, and/or RNA, and/or synthetic nucleotide analogs. Included within probes are "capture probes," "blocking probes," and "label probes."

The term "primer" or "nucleic acid primer" or "nucleic acid primer sequence" includes single-stranded oligonucleotides that, typically, are between about 4 to about 100 bases, or alternatively between about 17 to 30 bases, or alternatively 20 or more bases, and are designed to hybridize with a corresponding template nucleic acid. Primer molecules may be complementary to either the sense or the anti-sense strand of a template nucleic acid and are typically used as complementary pairs that flank a nucleic acid region of interest.

The term "polymerase" includes any one of, or a mixture of, the nucleotide polymerizing enzymes *E. coli* DNA polymerase I, Klenow fragment of *E. coli* DNA polymerase I, T4 DNA polymerase, reverse transcriptase where the template is RNA and the extension product is DNA, or a thermostable DNA polymerase. The term "thermostable DNA polymerase" includes a thermostable DNA polymerase isolated from *Thermus aquaticus, Thermus thermophilus, Thermus filiformis, Thermus flavus, Pyrococcus furiosus, Thermococcus literolis*, a *Thermotoga* species, or a recombinant form thereof.

The term "sample" or "biological sample" refers to a sample of tissue or fluid isolated from an individual, including but not limited to, blood, plasma, serum, spinal fluid, lymph fluid, the external sections of the skin, respiratory, intestinal, and genitourinary tracts, tears, saliva, milk, urine, blood cells, tumors, amniotic fluid, organs, genomic DNA, RNA, or cDNA in solution or bound to a substrate, and also samples of in vitro cell culture constituents including, but not limited to, conditioned medium resulting from the growth of cells in cell culture medium, putatively virally infected cells, recombinant cells, and cell components, e.g., chromosome (s), organelles, paraffin embedded tissues, or membranes isolated from a cell.

The "sense strand" of a nucleic acid contains the sequence that has sequence homology to that of mRNA. The "antisense strand" contains a sequence which is complementary to that of the "sense strand."

The term "target region" refers to a region of the nucleic acid that is to be amplified and/or detected. The term "target sequence" refers to a sequence with which a probe or primer will form a stable hybrid under desired conditions.

The term "targeting polynucleotide sequence" as used herein, refers to a polynucleotide sequence which is comprised of nucleotides which are complementary to a target nucleotide sequence; the sequence is of sufficient length and complementarity with the target sequence to form a duplex which has sufficient stability for the purpose intended.

HCV has at least six genotypes, and multiple subtypes within each genotype. Sequences which correspond to the HCV 1a and 1b subtype may be selected from SEQ ID NOS: 1-23 and SEQ ID NO:64, set forth in Tables 1A and 1G. Sequences which correspond to the HCV 2a subtype may be selected from SEQ ID NOS:24-27, set forth in Table 1B. Sequences which correspond to the HCV 2b subtype may be selected from SEQ ID NOS:28-42, set forth in Table 1C. Sequences which correspond to the HCV 3a subtype may be selected from SEQ ID NOS:43-46, set forth in Table 1D. Sequences which correspond to the HCV 3b subtype may be selected from SEQ ID NOS:47-50, set forth in Table 1E. Sequences which correspond to the HCV 4a subtype may be selected from SEQ ID NOS:51-63, set forth in Table 1F. The sequences of the invention, set forth as SEQ ID NOS:1-64, are defined in the Sequence Listing of the application.

In one embodiment, the oligonucleotides of the present invention are at least 80%, 81%, 82%, 83%, 84%, 85%, 86%, 87%, 88%, 89%, 90%, 91%, 92%, 93%, 94%, 95%, 96%, 97%, 98%, 99% or more identical to the nucleotide sequence set forth in SEQ ID NOS:1-64. In yet another embodiment, the nucleic acid molecule of SEQ ID NOS:1-64 is at least 4, 8, 10, 11, 12, 13, 14, 15, 16, 17, 18, 19, 20, or more nucleotides in length. It will be appreciated that the 5' end may contain greater variability (e.g., nucleic acid substitutions), yet remain functional (e.g., able to anneal to the NS3 and NS4 portion of the HCV genome).

The preparation of the nucleic acid sequences of the present invention is by means known in the art, including, for example, by methods which include excision, transcription, or chemical synthesis. The target sequences and/or regions of the genome which are selected to which the targeting nucleic acid sequence are complementary depend upon the purpose. For example, if the goal is to screen for the presence of HCV in biological samples (e.g., blood), the preferred nucleic acid sequence would be used as primers, and would hybridize to conserved regions of the HCV genome. Some of the conserved regions of the HCV genome to which the nucleic acid sequences of the present invention may bind are described herein. Other regions of the genome which are conserved are ascertainable by comparison of the nucleotide sequences of various isolates of HCV as described herein.

It will be appreciated that the nucleic acid sequences of the present invention need not consist only of the sequence which is complementary to the targeted HCV sequence. Thus, the nucleic acid sequences of the present invention may contain in addition, nucleotide sequences or other moieties which are suitable for the purposes for which the nucleic acid sequences are used. For example, use of the nucleic acid sequences as primers may be used for the amplification of HCV sequences via PCR, they may contain sequences which, when in duplex, form restriction enzyme sites which facilitate the cloning of the amplified sequences.

The nucleic acid sequences of the invention may be used as probes to detect the presence of HCV polynucleotides (for example in screening for contaminated blood), the biological sample to be analyzed, such as blood or serum, may be treated, if desired, to extract the nucleic acids contained therein. The resulting nucleic acid from the sample may be subjected to gel electrophoresis or other size separation techniques; alternatively, the nucleic acid sample may be dot blotted without size separation. In order to form hybrid duplexes with the targeting sequence of the probe, the targeted region of the nucleic acid must be in single stranded form. Where the sequence is naturally present in single stranded form, denaturation will not be required. However, where the sequence is present in double stranded form, the sequence will be denatured. Denaturation can be carried out by various techniques known in the art. Subsequent to denaturation, the analyte nucleic acid and probe are incubated under conditions that promote stable hybrid formation of the target sequence in the probe with the putative targeted sequence in the analyte, and the resulting duplexes containing the probe(s) are detected.

Detection of the resulting duplex, if any, is usually accomplished by the use of labeled probes; alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation or kinasing), radioactive isotopes, biotin, fluorescent groups, chemiluminescent groups (e.g., dioxetanes, particularly triggered dioxetanes), digoxigenin, enzymes, antibodies, luminescent agents, precipitating agents, dyes, and the like.

The amplified HCV nucleic acid sequences generated from the methods set forth herein may be cloned into a host vector with an expression promoter and used as a DNA vaccine to amplify a patient's response to the HCV virus, thereby providing a patient-specific DNA vaccine to HCV. In another embodiment, the clone may be used to generate RNA for use as an antisense vaccine. In one embodiment, an HCV vaccine is provided and employed as an immunotherapeutic agent for the prevention of HCV. In another embodiment, a HCV vaccine is provided and employed as an immunotherapeutic agent for the treatment of HCV.

By way of example, an HCV vaccine may be employed for the prevention and/or treatment of HCV in a subject by administering the vaccine by a variety of routes, e.g., intradermally, subcutaneously, or intramuscularly. In addition, the HCV vaccine can be administered together with adjuvants and/or immunomodulators to boost the activity of the vaccine and the subject's response. In one embodiment, devices and/or compositions containing the vaccine, suitable for sustained or intermittent release could be, implanted in the body or topically applied thereto for the relatively slow release of such materials into the body. The HCV vaccine can be introduced along with immunomodulatory compounds, which can alter the type of immune response produced in order to produce a response which will be more effective in eliminating the virus.

SPECIFIC EXAMPLES

Example 1

Genetic Diversity and Response to Interferon of the NS3 Protease Gene from the Clinical Strains of the Hepatitis C Virus This example describes an analysis of natural genetic diversity within the NS3 gene, wherein a nested PCR method was developed to obtain HCV NS3 sequence data directly from patient strains. The data was analyzed to determine overall genetic diversity, phylogeny of the virus, and selection of genetic variants by interferon therapy with or without ribavirin. The effects of genetic diversity on enzyme structure using molecular modeling were determined. Thus, a comprehensive approach was developed to facilitate analysis of natural genetic variation within this gene and its effects on protein structure.

The N-terminal one-third of the hepatitis C virus nonstructural gene 3 (NS3) codes for a serine protease (see FIG. 1 in Holland-Staley, C. A., et al., 2002, supra).

While genetic diversity has been shown to be extensive in other regions of the HCV genome such as the envelope region, the extent of diversity within the HCV NS3 protease region is largely unknown. Accordingly, the data set forth herein was used to determine the evolutionary rates of the virus and to identify the effects of mutations on enzyme structure. To investigate natural genetic diversity of this enzyme a nested PCR reaction was developed to obtain NS3 protease sequence data directly from patient strains. This data was used to determine genetic diversity, phylogenetic and evolutionary rates, and selection of variants by interferon therapy. The potential effect of genetic diversity on enzyme structure using molecular modeling was also attempted. In doing these experiments, a database of naturally occurring sequences has been established. This database is useful in the development of new antiviral therapy.

Genetic diversity among strains is important because of evidence that some HCV types are more pathogenic than others Cooreman, M. P. et al. (1996) Hepatitis C virus: biological and clinical consequences of genetic heterogeneity. *Scand J Gastroenterol Suppl* 218:106-115; Dusheiko, G. et al. (1994) Hepatitis C virus genotypes: an investigation of type-specific differences in geographic origin and disease. *Hepatology* 19:13-18; Stempniak, M. et al. (1997) The NS3 proteinase domain of hepatitis C virus is a zinc-containing enzyme. *J Virol* 71:2881-2886), i.e., HCV type 1 over other types, and subtype 1b over subtype 1a. The cause for increased pathogenesis in these strains is unclear. Describing differences among strains that have a rapid progression to disease in comparison to those which don't, will help to elucidate the possible cause and mechanisms of pathogenesis (Farci, P. et al. (2000) The outcome of acute hepatitis C predicted by the evolution of the viral quasispecies. *Science* 288:339-344). Recently, Yanagi et al. (Yanagi, et al. (1998) Transcripts of a chimeric cDNA clone of hepatitis C virus genotype 1b are infectious in vivo. *Virology* 244:161-172) showed that the number of mutations within the HCV genome can be directly related to infectivity. They chose three chimeric cDNA clones from the same source and inoculated chimpanzees. Of the three clones, only one was infective. This clone contained 3 amino acid substitutions when compared to the parent strain while the non-infective clones contained 7 and 9 amino acid substitutions. This may indicate a selection bias in chimpanzees due to immune system differences instead of an HCV strain characteristic (Bassett, S. E. et al. (1998) Analysis of hepatitis C virus-inoculated chimpanzees reveals unexpected clinical profiles. *J Virol* 72:2589-2599). In another study, when hypervariable region 1 was examined (Shindo, M. et al. T (1996) The clinical significance of changes in genetic heterogeneity of the hypervariable region 1 in chronic hepatitis C with interferon therapy. *Hepatology* 24:1018-1023) it was shown that higher amounts of heterogeneity were associated with a poorer overall response despite treatment with alpha-interferon. In addition, Chambers, T. J. et al. (Chambers, T. J. et al. (1991) Processing of the yellow fever virus nonstructural polyprotein: a catalytically active NS3 proteinase domain and NS2B are required for cleavages at dibasic sites. *J Virol* 65:6042-6050); established that mutations which affected activity of the NS3 protease from the Yellow Fever virus, were lethal for viral replication. The outcome of these studies affirms the need to further characterize the role that heterogeneity plays in HCV infection. The compositions and methods of the present invention provide a mechanism for such characterization.

Filocamo et al., 1999. Selection of functional variants of the NS3-NS4A protease of hepatitis C virus by using chimeric sindbis viruses. J Virol 73:561-575 used chimeric Sindbis viruses (SBV) to analyze variants of the NS3/NS4A protease, however, their study used a cloned protease and relied on the SBV replication machinery to produce sequence variation. While this allowed characterization of new protease variants, these variants may or may not represent those obtained from HCV replication in vivo. In addition, Forms et al. (Forms X., et al. (1997) How *Escherichia coli* can bias the results of molecular cloning: preferential selection of defective genomes of hepatitis C virus during the cloning procedure. *Proc Natl Acad Sci USA* 94:13909-13914) found when cloning PCR products of HCV structural proteins into *E. coli*, that a strong selection for defective clones occurred and accurate representation of true genetic diversity did not occur. The reason for this is unclear; however, toxicity to the *E. coli* host by viral proteins may play a role. Direct sequencing from patient samples should give a more accurate representation of true genetic diversity.

Most RNA viruses have a high mutation rate due to the lack of proofreading enzymes and because RNA-dependent RNA polymerases are thought to randomly produce one error per round of genomic replication (Drake, J. W. (1993) Rates of spontaneous mutation among RNA viruses. *Proc Natl Acad Sci USA* 90:4171-4175). Therefore, if there are $10^{7-8}$ viruses produced per day and the mutation rate is random, then each site will theoretically contain an equal number of mutations. The data set forth herein, however, showed that this was not the case, indicating that while the mutations were random, some regions of the virus are more permissive to mutations than other regions. This suggests that the virus, or at least the NS3 protease region, is subject to other functional constraints. The location of amino acid changes in the HCV NS3 protease from clinical strains indicates that amino acid substitutions take place in both the N- and C-terminal domains. It has already been demonstrated that the N-terminal domain of NS3 exhibits a structural plasticity upon NS4A binding. Kim, J. L. et al. (Kim, J. L. et al. (1996) Crystal structure of the hepatitis C virus NS3 protease domain complexed with a synthetic NS4A cofactor peptide. *Cell* 87:343-355) and; Yan, Y. et al. (Yan, Y. et al. (1998) Complex of NS3 protease and NS4A peptide of BK strain hepatitis C virus: a 2.2 A resolution structure in a hexagonal crystal form. *Protein Sci* 7:837-847) reported that the N-terminal domain is flexible since the binding of the NS4A leads to ordering on the N-terminal 28 residues and causes local rearrangements for a catalytically more favorable conformation of the active site. Activation of the NS3 protease by the NS4A peptide leads to a ~950-fold enhancement of catalytic hydrolysis of peptides mimicking the NS4A/NS4B junction (Yan. Y. et al. 1998 supra). Based on structural changes predicted from the sequences of clinical HCV strains, it is believed that there will be functional changes relative to the wild type protease. An example of such a change would be the alteration of the pseudo-second-order rate constant ($k_{cat}/K_M$) for the various clinical strains. A second observation is that structural variation of HCV NS3/NS4A complex ought to be factored into the structure-based design of the inhibitors in order to retain efficacy against a wide range of clinical isolates.

For patient strains 23 and 25, the differences in subtype designation between the 5' untranslated region and the NS3 protease region is unknown, but may occur due to the presence of more than one subtype. Simultaneous infection with multiple species of Dengue virus has been shown to occur (Gubler, D. J. et al. (1985) A case of natural concurrent human infection with two dengue viruses. *Am J Trop Med Hyg* 34:170-173). For HCV infection, this is most likely due to multiple blood transfusions or infections through IVDA. Because HCV subtypes 1a and 1b are most predominant in this geographical distribution, the likelihood that they would recombine increases. Evidence of recombination has been shown in Dengue virus, where genetic diversity occurs when the RNA polymerase switches between two different genomes during replication, resulting in a hybrid RNA (Holmes, E. C. et al. (2000) The causes and consequences of genetic variation in dengue virus. *Trends Microbiol* 8:74-77). This may be the case with strains 23 and 25, where they typed as HCV1a based on the 5' untranslated region, but closer to the HCV1b clade by the NS3 protease nucleotide sequence. The sequence results were clean, and did not show evidence of more than one species, suggesting recombination occurred prior to the start of NS3. Amino acid sequence comparison, however, showed very different results. Patient 23 had 3 mutations when compared to the type 1a consensus and 16 mutations when compared to the type 1b consensus. Patient 25 showed similar results with 4 mutations when compared to type 1a and 16 when compared to type 1b. The differences between nucleotide sequence analysis and protein analysis is unknown. Without being limited by theory, it is believed that these two strains represent a new subtype, which falls on the evolutionary tree between subtypes 1a and 1b.

This example revealed that there is significant variability in clinical HCV strains at both the nucleotide (30.2% for 1a and 25.8% for 1b) and amino acid sequences (12.2% for 1a and 12.2% for 1b). Phylogenic analysis showed two distinct clades with two HCV isolates grouping as a sister clade to 1b. Moreover, structural analysis revealed that most mutations lie in the N-terminus of the enzyme. When strains were sorted as to whether or not the patient had received antiviral therapy, no difference was found in the number or locations of mutations in 1a strains. However, 1b strains demonstrated an overall drop in the number of positions that were mutated. Thus, this study demonstrated that there are significant differences among natural strains that may pose a problem for structure-based drug development, for which this invention provides a solution.

The relationship between sequence variation and structural changes in the HCV NS3/NS4A complex can also be done by X-ray crystallography. Based on the compositions and methods of the present invention, anti-viral, including anti-HCV, drugs can be designed and developed with knowledge of the variability in the structure in the NS3/NS4A complex from HCV clinical strains to ultimately develop effective therapies against HCV.

Materials and Methods

Extraction of Viral RNA.

HCV RNA was isolated from patient serum using the QIAamp viral RNA mini isolation kit (Qiagen Inc., Valencia, Calif.). Isolation was performed according to manufacturers directions.

RT-PCR and Amplification of Viral RNA.

The Reverse Transcriptase-Polymerase Chain Reaction (RT-PCR) followed by a $2^{nd}$ round 'nested' PCR reaction was used to amplify the entire NS3 gene of HCV subtypes 1a or 1b, from clinical strains. For the RT-PCR step, the Promega Access Reverse Transcriptase PCR kit (Promega Corporation, Madison, Wis.) was used. For this, two oligonucleotide primers flanking the HCV NS3 gene were designed. The 5' primer set forth in SEQ ID NO:1 anneals 881 bp before the start of the NS3 gene. The 3' primer set forth in SEQ ID NO:2 anneals 338 bp downstream of NS3 and is used to initiate the RT step (Table 1G, SEQ ID NOS:1-4, SEQ ID NO:64 and SEQ ID NO:6, "Amplification" subsection). This allows cDNA production followed by initial amplification of the desired region. The amplification mixture containing 25 pmol of each primer, 200 μM dNTPs, 2.5 U AMV RT-polymerase, 2.5 U Tfl DNA polymerase, 1.5 mM MgSO$_4$, and 20 μl of viral RNA was added to a preheated (48° C.) Perkin-Elmer 9700 thermocycler (Perkin Elmer Cetus, Foster City, Calif.). The PCR protocol consisted of an RT step at 48° C. for 45 minutes, followed by an initial denaturation at 94° C. for 2 minutes, and 35 cycles of, 94° C. for 15 seconds; 55° C. for 20 seconds; 72° C. for 2 minutes; and a final extension at 72° C. for 10 minutes.

For the second step PCR reaction, the $1^{st}$ round PCR product was amplified using primers that anneal inside the previous reaction, creating a 'nested' amplification. The second round PCR reaction used the 5' primer set forth as SEQ ID NO:3 which anneals 693 bp upstream of NS3 and the 3' primer set forth as SEQ ID NO:4 which anneals 161 bp downstream. The amplification mixture containing 25 pmol of each primer, 200 µM dNTPs, 2.5 U Taq© DNA polymerase, 1.5 mM MgSO$_4$, and 5 µl of 1st round product was added to a preheated (94° C.) thermocycler. Initial denaturation consisted of 10 minutes at 94° C., followed by 35 cycles of, 94° C. for 15 seconds; 55° C. for 20 seconds; 72° C. for 2 minutes and a final extension at 72° C. for 10 minutes. The resulting amplification product is a single 2746 bp band on a 1% agarose gel. The entire NS3 gene was amplified using this method, however, only the NS3 protease gene is characterized herein. Second step reaction products were purified and concentrated using the Gene Clean Spin Protocol (Bio 101, Vista, Calif.). Purified products were used directly for DNA sequencing. To ensure that each HCV RNA isolation was successful, primers which cover the highly conserved 5'-untranslated (5'-UTR) region were used as a control (Yuki, N. et al. (1997) Hepatitis C virus replicative levels and efficiency of genotyping by specific PCR and antibody assay. *J Clin Microbiol* 35:1184-1189). PCR products from this control region were also purified as set forth above and sequenced. Sequence data from the 5'UTR region were then used to genotype each HCV strain (O'Brien, C. B. et al. D (1997) cDNA sequencing of the 5' noncoding region (5' NCR) to determine hepatitis C genotypes in patients with chronic hepatitis C. *Digestive Diseases and Sciences* 42:1087-1093). If the second round PCR amplification was unsuccessful, a new round of amplification using a second set of internal 'backup' primers was performed. The 5' backup primer set forth as SEQ ID NO:64 and the 3' backup primer set forth as SEQ ID NO:6 result in a 2377 bp amplification product, which truncates the NS3 gene (helicase region) by 19 bp.

DNA Sequencing.

Sequencing of purified second step PCR reaction products was performed using the ABI Big Dye Terminator technology (Applied Biosystems, Foster City, Calif.). Five primers set forth as SEQ ID NOS:7-11 (see Table 1G, "Sequencing" subsection) designed to cover the NS3 protease region on both the sense and anti-sense strands were used. For ABI analysis, sequence reactions were run in microtiter plates using a thermocycler for 25 cycles of 96° C. for 10 seconds; 50° C. for 5 seconds; and 60° C. for 4 minutes. Reaction products were NaOAc/ETOH purified, resuspended in loading buffer, denatured and run on an ABI 377 sequencer (Applied Biosystems).

Sequence Analysis.

ABI sequence results were analyzed using the ABI sequence analysis software version 3.3. Individual sequences were aligned against a consensus derived from all patient sequence data and against HCV types 1a and 1b (Accession Numbers AF009606 and AJ000009) (Yanagi, M. et al. (1997) Transcripts from a single full-length cDNA clone of hepatitis C virus are infectious when directly transfected into the liver of a chimpanzee. *Proc Natl Acad Sci USA* 94:8738-8743; and Yanagi, M. et al., (1998). Transcripts of a chimeric cDNA clone of hepatitis C virus genotype 1b are infectious in vivo. *Virology* 244:161-172). The two Genbank sequences were chosen for comparison because they are available as cloned constructs for use as positive controls for subsequent protein expression assays (data not shown). Amino acids that differ from the consensus are compared and used to determine which residues are conserved or variable.

Phylogenetic Analysis.

Sequences were aligned using Sequencer 3.0, and the multiple alignment was exported as a Nexus file. Parsimony analysis was run using PAUP 3.1.1 (Swofford, D. L. (1993) *PAUP: Phylogenetic analysis using parsimony*. 3.1 ed. Illinois Natural History Survey, Champaign, Ill.) with a heuristic search with branch swapping. For comparison, a branch and bound option was also used to search for the most parsimonious trees. A distance matrix based on Kimura Two-Parameter distances was generated using the DNADIST program of PHYLIP Version 3.573c (Felsenstein, J. (1993) *PHYLIP* (phylogenetic Inference Package), 3.5p ed. Department of Genetics, University of Washington, Seattle). A two to one transition to transversion ratio was used. The distance matrix was then analyzed by Neighbor-Joining Analysis (NJ) using the NEIGHBOR program in PHYLIP. Bootstrap support analysis was executed using 1000 resamplings for both NJ and Parsimony Analyses. The multiple data sets for the NJ were generated by the SEQBOOT program and the multiple trees were determined for consensus by the CONSENSE program, both in PHYLIP. The Parsimony bootstrap was completed using the bootstrap option in PAUP.

The number of segregating sites for each population was counted from the Sequencher 3.0 generated multiple alignments. The distinction of synonymous versus non-synonymous substitutions was made based on proposed translations of the sequences. Population mutation parameter $\theta=2N\mu$ was estimated following Watterson (Watterson, G. A. (1975) On the number of segregating sites in genetical models without recombination. *Theoretical Pop Biol* 7:256-276). Tests of neutrality follow McDonald and Kreitman (McDonald, J. et al. (1991) Adaptive protein evolution at adh locus in *Drosophilia*. *Nature* 351:652-654).

Homology Protein Structure Modeling.

Homology protein structure modeling by satisfaction of spatial restraints was performed according to the method of Sali, et al., 1995 (Sali, A. (1995) Comparative protein modeling by satisfaction of spatial restraints. *Mol Med Today* 1:270-277). Homology protein structure modeling is founded on building a structural model of a protein on the basis of close similarity to a template protein of known structure.

In the first stage of protein structure modeling, the alignment between the unknown sequence and related template structures were obtained. Secondly, restraints on various distances, angles, and dihedral angles in the sequence were derived based on its alignment with the template structures. Finally, the three dimensional models were obtained by minimizing violations of homology-derived and energy restraints, using conjugate gradients and molecular dynamics procedures. An important step in homology protein modeling experiments is the evaluation of the model quality. To ensure the quality, internal consistency checks as implemented in the software package MODELLER 4 (Sali, A. et al. (1993) Comparative protein modelling by satisfaction of spatial restraints. *J Mol Biol* 234:779-815) were used to test the three-dimensional profile.

The comparative protein modeling software package MODELLER was used to calculate the structures of the HCV NS3/NS4 complex. This software package has been tested extensively in structural genomics projects by Sanchez and Sali, 1998 (Sanchez, R. et al. (1998) Large-scale protein structure modeling of the *Saccharomyces cerevisiae* genome. *Proc Natl Acad Sci USA* 95:13597-13602). The 2.2 Å crystal structure of the complex of the HCV NS3 protease and NS4A peptide (Yan, Y. et al. 1998, supra) was used as a template for the homology modeling experiments to examine structural changes in the HCV NS3 protease clinical strains. The crystal structure of the HCV NS3/NS4A complex and the modeled structures of the HCV NS3/NS4A proteases were least-squares superimposed using the program suite O (Jones, T. A. et al. (1991) Improved methods for building protein models in electron density maps and the location of errors in these models. *Acta Cryst* A47:110-11932.

Optimization of the HCV NS3/NS4A models was carried out using default settings in MODELLER 4.0 (number of iterations in optimization=200; non-bonded restraint type=dynamic soft-sphere repulsion terms). The model is obtained by optimizing an objective function (combined spatial restraints and CHARMM energy terms enforcing proper stereochemistry) in Cartesian space.

Nucleotide Sequence GenBank Accession Numbers.

The nucleotide sequences described herein have been deposited with the American Type Culture Collection (ATCC), 10801 University Boulevard, Manassas, Va. 20110-2209, on Apr. 9, 2001 and assigned Accession Numbers AF369214 through AF369263. These deposits will be maintained under the terms of the Budapest Treaty on the International Recognition of the Deposit of Microorganisms for the Purposes of Patent Procedure. These deposits were made merely as a convenience for those of skill in the art and is not an admission that a deposit is required under 35 U.S.C. §112.

Results

Patient Population.

Serum from thirty patients infected with HCV subtypes 1a or 1b was analyzed. Eighteen men and twelve women with a mean age of 50.2 years (range, 21-76) were included. Nineteen were treatment-naïve, while the remaining 11 had treatment with either α-IFN alone (patients 11, 183 and 205), α-IFN+ribavirin (pt. 176) or an initial course of α-IFN followed by a second round of combination therapy (patients 252, 174, 186, 1D, 1Y, 179, 25). All patients received 3 million units, 3× a week for 12 months except patients 11 and 205, who received a second course of α-IFN therapy of 5 million units 4× a week, and 1.5 million units 3× a week, respectively, and patients 186 and 1Y, who had therapy stopped after 6 months. No one had a sustained response. All patients had HCV RNA viral loads of between $5.1 \times 10^4$ and $2.3 \times 10^6$ copies/ml as determined by using the Roche Amplicor® HCV Monitor Test.

Genotyping.

The conserved 5' untranslated region was sequenced to place each strain into the respective genotype using the method of O'Brien et al. (O'Brien, C. B. et al. (1997) cDNA sequencing of the 5' noncoding region (5' NCR) to determine hepatitis C genotypes in patients with chronic hepatitis C. *Digestive Diseases and Sciences* 42:1087-1093). Genotype results showed that 21 sequences were HCV subtype 1a and 9 were subtype 1b. These data are consistent with the patient population, with HCV subtypes 1a and 1b being the most prevalent in this region of the world. The data set forth herein demonstrates a correlation between the 5'-UTR genotype and NS3 sequence data.

Amplification and Sequencing the NS3 Region from Clinical Strains.

The NS3 protease gene has been successfully sequenced and amplified herein from the sera of 30 patients infected with HCV subtypes 1a or 1b. The amplification product produced a clean band with a success rate of >80% (FIG. 1). The resulting sequences were then translated and a consensus sequence was derived from the alignment of all patient sequences. Each patient sequence was compared to the consensus sequence and against the prototype sequences found in Genbank for each subtype (Genbank #AF009606 & #AJ000009) (Yanagi, M. et al., 1998, supra; see also Yanagi, M. et al., 1998, supra). The variable and conserved regions within these sequences were then determined for both nucleotide and amino acid residues.

Analysis of Nucleotide Sequence.

There are 543 nucleotides that encode the NS3 protease gene. Sequence data was analyzed to determine the nucleotide distribution at each position when compared to the patient derived consensus sequence and the two prototype sequences from Genbank. For those strains belonging to HCV subtype 1a, 164 positions contained one or more nucleotide substitutions when compared to the patient consensus sequence, resulting in an overall sequence variation of 30.2% (data not shown). These included 133 transitions, 9 transversions and 22 sites with both transitions and tranversions. When compared to the prototype 1a, 20 positions were different (overall sequence variation of 3.5%), with 17 positions containing transitions and 3 containing transversions (Table 2A). There were no detected insertions or deletions. For strains typing as HCV subtype 1b, 140 positions contained one or more substitutions when compared to the patient consensus sequence, for an overall sequence variation of 25.8%. There were 114 transitions, 8 transversions and 18 sites containing both transitions and tranversions. There were 38 positions that varied from the prototype 1b sequence (overall 7.4%), with 34 transitions and 4 transversions (Table 2B). Insertions or deletions were not detected in any sequences. Without being bound by theory, because the predicted mutation rate introduced during PCR amplification was ~0.1%, it is believed that the data portrays an accurate representation of natural genetic sequence variation.

Analysis of Amino Acid Sequence.

There are 181 amino acids that comprise the NS3 protease. The effects of nucleotide substitution on the amino acid sequence showed that most of the substitutions were silent. For the 21 patient sequences belonging to HCV subtype 1a, 22 residues or 12.2% differed from the patient strain consensus (Table 3). The prototype sequence differed from the patient consensus by 5 residues (A40T, K80Q, A91S, I153L, E176G) including one mutation not found in any patient sequences (underlined). Three sites had more than two amino acid species present (Vizmanos, J. L. et al., 1998, supra; Yanagi, M. et al. (1997) Transcripts from a single full-length cDNA clone of hepatitis C virus are infectious when directly transfected into the liver of a chimpanzee. *Proc Natl Acad Sci USA* 94:8738-8743), and one site (residue 86) was able to tolerate 4 different residues. Including the control sequence, 9 sites had substitutions of the same amino acid type, 9 sites were able to accommodate either neutral or polar amino acids, 3 sites basic or polar, 2 sites acidic or polar, and one site acidic or neutral. Only two strains were identical to the consensus with no amino acid substitutions (K and 161).

For patient strains that typed as HCV1b, there was an overall sequence variation of 12.2%, with 22 sites different from the patient derived consensus (Table 4). The patient consensus differed from the prototype sequence by 8 residues (L13V, V48I, Q80L, L94M, T98S, A150V, I153V, V170I) including 4 sites not previously identified (underlined), bringing the total number of sites containing one or more amino acids to 26. More than two amino acid species were present in 2 sites (61 and 80), and residue 67 had up to 4 different residues (residue 86 did not contain any mutations). The same type of substitution was seen in eleven sites, 8 sites accommodated either neutral or polar amino acids, 1 site basic or polar, 2 sites basic or neutral and the remaining site had an amino acid change neutral to aromatic. Only strain 153 was identical to the consensus. For either types 1a or 1b no amino acid substitutions at the known conserved residues were found.

Selection by Interferon Therapy.

The most significant differences were noticed when strains were grouped according to whether or not the host had received interferon therapy. For strains that had not been subjected to interferon therapy with or without ribaviron, the overall number of mutations per patient averaged 1.9 for type 1a strains, with 14 sites containing mutations. After interferon therapy, the number of mutations per patient averaged 2.6 with 15 sites containing different amino acids. Only 7 sites were similar both before and after therapy (Table 3). For type 1b strains, the average number of mutations per patient for strains not subjected to interferon therapy was 3.6 with 18 sites varying overall. However, after interferon therapy, while the number of mutations per patient were not significantly different (3.0), the number of sites which contained mutations in the 1b strains dropped to 10, or by 56% (Table 4) with 6 sites similar in strains with or without therapy. This suggests that the sensitive strains were eliminated during interferon therapy and these 10 remaining sites may somehow be involved in resistance of the virus to interferon.

In summary, the most frequently occurring amino acid changes are represented by hydrophobic to hydrophobic amino acid mutations followed by positively charged to neutral side chain changes. The rate of mutations from a more bulky to less bulky amino acid side chain occurs at a higher rate than vice versa. In type 1b strains, sequence diversity in the NS3 protease is significantly reduced in strains from patients who have undergone IFN therapy. This suggests that sensitive strains are eliminated during interferon therapy and those strains that remain after therapy may be less sensitive to the drug.

Phylogenetic Analysis and Molecular Evolution.

Figure 2A:
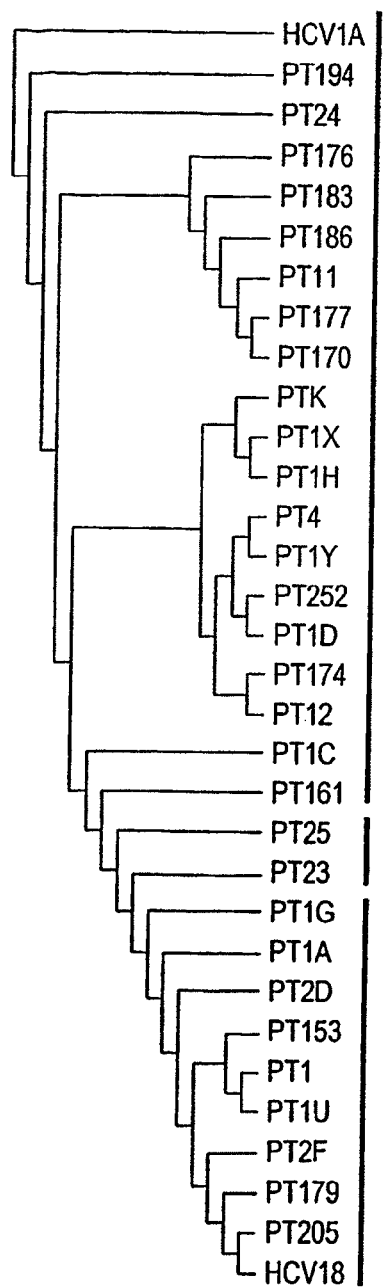
FIGS. 2A-2B depict phylogenetic trees constructed from 30 HCV NS3 protease strains using Parsimony Analysis and Neighbor-joining.

Parsimony analysis using a heuristic search with branch swapping detected 141 equally parsimonious trees with 696 steps. A comparable branch and bound option detected 144 equally parsimonious trees with 696 steps. The sequences are grouped in over 95% of the trees into two clades, the HCV1a and HCV1b clades. The HCV1a clade consists of 19 strains (K, 4, 11, 12, 24, 161, 170, 174, 176, 177, 183, 186, 194, 252, 1C, 1D, 1H, 1X, and 1Y) instead of 21 as identified with genotyping. The remaining samples (1, 23, 25, 153, 179, 205, 1A, 1G, 1U, 2D, and 2F) grouped with HCV1b. These results are strongly supported in the bootstrap analysis, although hierarchical relationships within the two clades are not strongly supported (FIG. 2A). In particular, FIG. 2A depicts a consensus tree of the parsimony analysis. The branch lengths are drawn to match hierarchal groups and do not reflect the mutational steps among strains. Within the HCV1b clade, the two strains 23 and 25 are sister taxa to the remaining strains. These two samples, 23 and 25, grouped with type HCV1a by genotyping and comparison of amino acid sequences.

Figure 2B:
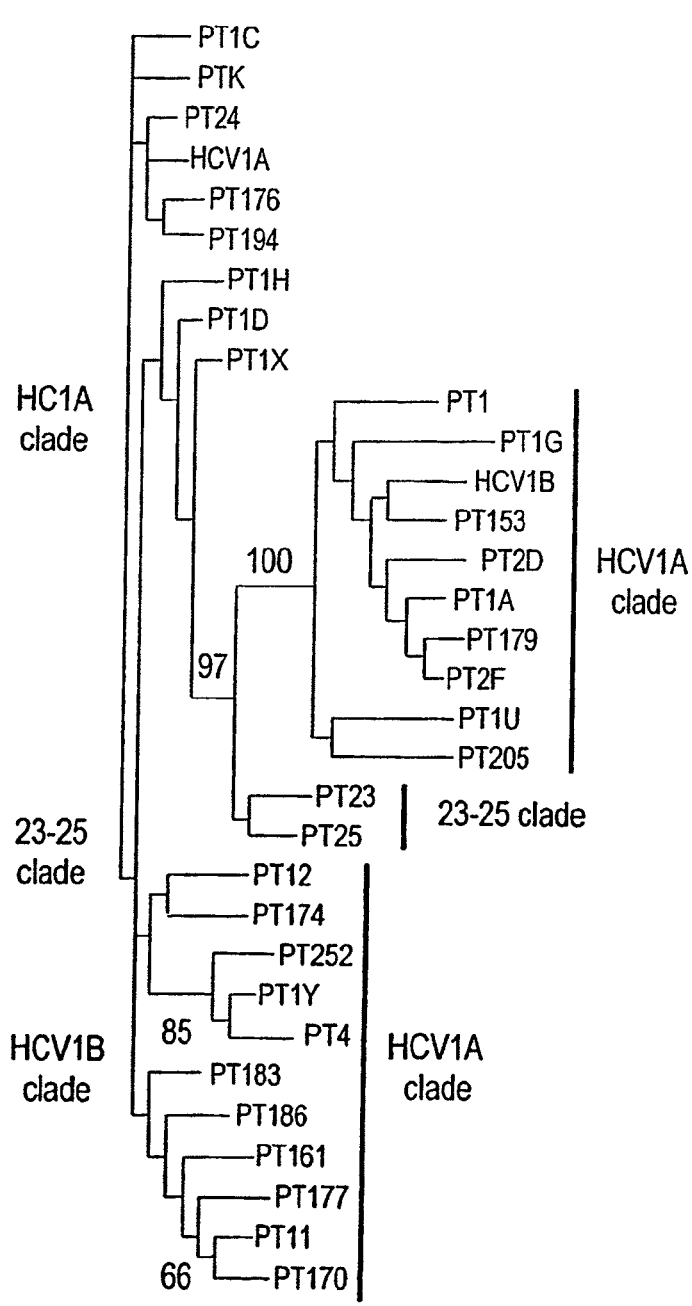

FIG. 2B depicts a bootstrap tree from the Neighbor-joining analysis. The Neighbor-Joining analysis produced very similar results to the parsimony analysis indicating a well-separated HCV1b clade consisting of strains 1, 1G, 153, 2D, 1A, 179, 2F, 1U, and 205 (FIG. 2B). Bootstrap support of the clades, as set forth herein, are indicated next to their appropriate branches. In addition, branch lengths are scaled to genetic distances.

Strains 23 and 25 group again as a sister lineage to the HCV1b clade. These data, along with the amino acid data, suggest their representation of a genetically differentiated third clade. Hierarchical relationships within the two major clades differ somewhat from that of the consensus Parsimony tree, but none of the differences are strongly supported in the NJ bootstrap. The HCV1b clade is supported in 100% of the bootstrap samplings. The separated 23-25 grouping is supported in 97.4% of the bootstrap samplings. Within the HCV1a clade, strains 4 and 1Y are monophyletic with 84.9% support, and 11, 170, and 177 are monophyletic with 66% support.

Analysis of Evolutionary Rates.

Population rates of evolution for the three lineages were estimated following (Watterson, G. A., 1975, supra). The estimators of θ (±S.D.) for HCV1a, HCV1b, and PT's 23-25 are 42.28±53.77, 49.49±61.81, and 40±40.50, respectively. Thus, there is no indication of differential rates of evolution occurring among the three lineages. Tests of non-neutral evolution between the two major lineages HCV1a and HCV1b were executed using the method of McDonald and Kreitman (McDonald, J. et al. (1991) Adaptive protein evolution at adh locus in *Drosophilia*. *Nature* 351:652-65441). Under neutrality, the ratio of synonymous and non-synonymous segregating sites should be constant within and among populations. In comparisons of the HCV1a and HCV1b populations, the $X^2$ value is 2.30 indicating no significant deviation from neutral expectations for sequence deviation among the two populations.

Molecular Modeling.

Protein homology modeling experiments of HCV NS3 protease/NS4A complex were carried out with the 2.2 Å crystal structure template of the NS3 protease and NS4A peptide of (Yan, Y. et al., 1998, supra); to examine three-dimensional changes due to sequence variation in clinical strains. The most divergent strains were selected for modeling. The focus was on subtypes A and B and, therefore, two highly divergent subtype 1A and two sequence-wise very different isolates belonging to subtype 1B were selected for these studies. Four clinical strains (252, 1G, 1H, and 1U) have been selected for modeling experiments. Two of the strains (252 and 1H) belong to subtype 1a and the other two strains (1G and 1U) belong to subtype 1b. Mutations occur most frequently in loop regions or at the termini of β-strands. Mutations also occur in the α-helices of NS3.

Homology models for the HCV1a or HCV1b consensus sequences using the crystal structure the NS3/NS4A complex of (Yan, Y. et al., 1998, supra) were computed with the program suite MODELLER. The models for the 1a and 1b consensus were superimposed for detailed analysis (see FIG. 4 in Holland-Staley, C. A., et al., 2002, supra), which indicates the largest differences between the two subtypes. Moreover, there were noticeable differences both in the active site and at other positions. There are distinguishable differences in the positions of the three residues of the catalytic triad, Asp81, His57 and Ser139. The modeling results suggest functional differences for the two subtypes.

The models from HCV clinical strains 252, 1G, 1H, and 1U which contain multiple amino acid changes were superimposed on the crystal structure of the wild type NS3/NS4A complex of Yan, Y. et al., 1998, supra. The NS3/NS4A complex of strain 1G was compared with the wild type crystal structure (see FIG. 5 in Holland-Staley, C. A., et al., 2002, supra). There are distinguishable differences in the positions of the three residues for the catalytic triad (Asp81, His57 and Ser139). Similar potential differences have been observed for strains 252, 1H and 1U (data not shown) (Holland-Staley, C. A., et al. (2002) Genetic diversity and response to IFN of the NS3 protease gene from clinical strains of the hepatitis C virus. *Arch Virol* 147:1385-1406), which is incorporated herein by reference.

Example 2

A Decrease in Genetic Diversity within the NS3 Helicase Gene from Clinical Isolates of the Hepatitis C Virus Correlates with Interferon Therapy This example describes the effects of interferon therapy (with or without ribaviron) on the NS3 helicase gene from patients infected with HCV type 1a or 1b. To do this, a nested PCR reaction was developed, which allows recovery of HCV NS3 sequence data directly from patient isolates. To analyze the effects of IFN therapy, a patient derived consensus sequence was made and used to determine the overall number of mutations in each clinical isolate. Then the sequences were grouped by whether or not the patient had IFN therapy (naïve vs experienced), and analyzed the number of positions which were mutated. These mutations were also used to predict response to IFN. The results demonstrate that a significant decrease in overall sequence variability occurs in those isolates which had been subjected to IFN therapy. Thus, the present invention provides a method to analyze the effects of IFN on the HCV NS3 gene and determine its effects on the quasispecies population.

Materials and Methods

Patient Samples and Extraction of Viral RNA.

Serum from forty three patients infected with HCV subtypes 1a or 1b was analyzed. Twenty three men and twenty women with a mean age 51.1 years (range, 21-76) were included. Twenty-nine were treatment naïve, while the remaining 14 had treatment with interferon alone or combined with ribaviron. All patients had HCV RNA viral loads of between $5.1\times10^4$ and $2.3\times10^6$ virions/ml as determined by using the Roche Amplicor® HCV Monitor Test. HCV RNA was isolated from patient serum using the QIAamp viral RNA mini isolation kit (Qiagen Inc., Valencia, Calif.). Isolation was performed according to manufacturers directions.

RT-PCR and Amplification of Viral RNA.

The Reverse Transcriptase-Polymerase Chain Reaction (RT-PCR) followed by a $2^{nd}$ round 'nested' PCR reaction was used to amplify the entire NS3 gene of HCV subtypes 1a or 1b, from clinical isolates. The RT-PCR step used the Promega Access Reverse Transcriptase PCR kit (Promega Corporation, Madison, Wis.). For this, two oligonucleotide primers flanking the gene were designed. The 5' primer (SEQ ID NO: 3) anneals 693 bp before the start of the NS3 gene. The 3' primer (SEQ ID NO: 2) anneals 338 bp downstream of NS3 and is used to initiate the RT step. This allows cDNA production followed by initial amplification of the desired region. The amplification mixture containing 25 pmol of each primer, 200 μM dNTPs, 2.5 U AMV RT-polymerase, 2.5 U Tfl DNA polymerase, 1.5 mM $MgSO_4$, and 20 μl of viral RNA was added to a preheated (48° C.) Perkin-Elmer 9700 thermocycler (Perkin Elmer Cetus, Foster City, Calif.). The PCR protocol consisted of an RT step at 48° C. for 45 minutes, followed by an initial denaturation at 94° C. for 2 minutes, and 35 cycles of, 94° C. for 15 seconds; 55° C. for 20 seconds; 72° C. for 2 minutes; and a final extension at 72° C. for 10 minutes.

For the second step PCR reaction, the $1^{st}$ round PCR product was amplified using primers, which anneal inside the previous reaction, creating a 'nested' amplification. The second round PCR reaction used the 5' primer (SEQ ID NO: 3) and the 3' primer (SEQ ID NO: 4). The amplification mixture containing 25 pmol of each primer, 200 μM dNTPs, 2.5 U Taq© DNA polymerase, 1.5 mM $MgSO_4$, and 5 μl of 1st round product was added to a preheated (94° C.) thermocycler. Initial denaturation consisted of 10 minutes at 94° C., followed by 35 cycles of, 94° C. for 15 seconds; 55° C. for 20 seconds; 72° C. for 2 minutes and a final extension at 72° C. for 10 minutes. The resulting amplification product is a single 2219 bp band on a 1% agarose gel. The entire NS3 gene was amplified using this method, however, only the NS3 helicase gene is characterized here. Second step reaction products were purified and concentrated using the Gene Clean Spin Protocol (Bio 101, Vista, Calif.). Purified products were used directly for DNA sequencing. To ensure each HCV RNA isolation was successful, primers which cover the highly conserved 5'-untranslated (5'-UTR) region were used as a control (Yuki, 1997 #226). PCR products from this control region were also purified as above and sequenced. Sequence data from the 5'UTR region were then used to genotype each HCV isolate (O'Brien, 1997 #30). If amplification was unsuccessful, a new round of RT-PCR was performed using a second 3' 'backup' primer. The 3' backup primer (SEQ ID NO: 6) results in a 2039 bp amplification product, which truncates the NS3 gene by 20 bp.

DNA Sequencing.

Sequencing of purified second step PCR reaction products was performed using ABI Big Dye Terminator technology (Applied Biosystems, Foster City, Calif.). Eleven primers (A-K) designed to cover the NS3 helicase region on both the sense and anti-sense strands were used. The sense primers are: A (SEQ ID NO: 9), B (SEQ ID NO: 12), C (SEQ ID NO: 15), D (SEQ ID NO: 13), E (SEQ ID NO: 17), F (SEQ ID NO: 18). Antisense primers are: G (SEQ ID NO: 10), H (SEQ ID NO: 14), I (SEQ ID NO: 16), J (SEQ ID NO: 6), K (SEQ ID NO: 4). For ABI analysis, sequence reactions were run in microtiter plates using a thermocycler for 25 cycles of 96° C. for 10 seconds; 50° C. for 5 seconds; and 60° C. for 4 minutes. Reaction products were NaOAc/ETOH purified, resuspended in loading buffer, denatured and run on an ABI 377 sequencer (Applied Biosystems).

Sequence Analysis.

ABI sequence results were analyzed using the ABI sequence analysis software version 3.3. Individual sequences were aligned against a consensus derived from all patient sequence data and against HCV types 1a (Accession Number AF009606) and 1b (Accession Number AJ00009) deposited in Genbank (Yanagi, 1997 #227) (Yanagi, 1998 #228). The two Genbank sequences were chosen for comparison because they are available as cloned constructs for use as positive controls for subsequent protein expression assays (data not shown). Amino acids that differ from the consensus are compared and used to determine which residues are conserved or variable.

Nucleotide Sequence GenBank Accession Numbers.

The nucleotide sequences described herein have been deposited with the American Type Culture Collection (ATCC), 10801 University Boulevard, Manassas, Va. 20110-2209, on Apr. 9, 2001 and assigned Accession Numbers AF369214 through AF369263. These deposits will be maintained under the terms of the Budapest Treaty on the International Recognition of the Deposit of Microorganisms for the Purposes of Patent Procedure. These deposits were made merely as a convenience for those of skill in the art and is not an admission that a deposit is required under 35 U.S.C. §112.

Results

Sequence Analysis of the HCV NS3 Helicase Gene.

A nested PCR reaction was used to amplify and sequence the HCV NS3 helicase gene from the sera of 43 patients infected with HCV subtypes 1a or 1b. The conserved 5' untranslated region was used to place each isolate into the respective genotype using the method of O'Brien et al. Genotype results show that 30 sequences were HCV subtype 1a and 13 were subtype 1b. These data are consistent for the patient population, with HCV subtypes 1a and 1b being the most prevalent in this region of the world. From the NS3 sequence data, a patient-derived consensus sequence was generated and used to determine the genetic variability of the patient isolates for both nucleotide distribution and amino acid substitution.

Within the sequences analyzed, significant variation in nucleotide and amino acid sequence was identified. There are 1350 nucleotides which encode the NS3 helicase gene. Sequence data was analyzed to determine the nucleotide distribution at each position when compared to the patient derived consensus sequence and the two prototype sequences from Genbank (Genbank #AF009606 & #AJ000009). For those isolates belonging to HCV subtype 1a, 436 positions contained one or more nucleotide substitutions when compared to the patient consensus sequence, resulting in an overall sequence variation of 32.30%. These included 355 (26.30%) transitions, 30 (2.22%) transversions and 51 (3.78%) with both transitions and tranversions. The HCV1a prototype differed at 34 positions (overall sequence variation of 2.52%), with 30 positions containing transitions and 4 containing transversions. No insertions or deletions were detected in either the patient sequences or the prototype. For isolates typing as HCV subtype 1b, 390 positions contained one or more substitutions when compared to the patient consensus sequence, for an overall sequence variation of 28.89%. There were 309 (22.89%) transitions, 36 (2.67%) transversions and 45 (3.33%) containing both transitions and tranversions. There were 55 positions in the HCV 1b prototype sequence that were different than the patient-derived consensus, with an overall sequence difference of 4.07%, with 47 transitions and 8 transversions. Insertions or deletions were not detected in any sequences. Since the predicted mutation rate introduced during PCR amplification is ~0.1%, it is believed that the data presented herein portrays an accurate representation of natural genetic sequence variation.

There are 450 amino acids that comprise the NS3 protease. The effects of nucleotide substitution on the amino acid sequence showed that most of the substitutions were silent. For the 30 patient sequences belonging to HCV subtype 1a, 65 residues or 14.44% differed from the patient-derived consensus (Table 5A). The published sequence differed from the patient consensus by 5 residues. Most sites had a single species substitution, 6 sites had three amino acid species present, with 2 sites (residues 334 & 383; numbering within NS3) able to tolerate 4 different residues. Including the control sequence, 38 sites had substitutions of the same amino acid type, 20 sites were able to accommodate either neutral or polar amino acids, 2 sites basic or polar, 2 sites acidic or polar, 1 site basic or neutral, 1 site acidic or neutral, and 1 site basic, polar or neutral. Only 1 patient (pt. 186) was identical to the consensus with no amino acid substitutions. Table 5A summarizes those mutations which occur in more than one patient sequence.

For patient isolates which typed as HCV 1b, there was an overall sequence variation of 11.33% with 51 sites different from the patient derived consensus (Table 5B). The patient consensus differed from the GenBank sequence by 13 residues, including 4 new residues, bringing the total number of sites containing one or more amino acids to 55 or 12.22% sequence variation. Three amino acid species were present in 9 sites, with residue 402 able to have 5 different amino acids and residue 470 having 7 different amino acids. The same type of amino acid substitution was seen in 26 sites, while, 20 sites were able to accommodate either neutral or polar amino acids, 5 sites basic or polar, 1 site acidic or polar, 1 acidic or basic and two sites could accommodate neutral or polar or basic amino acids (Table 5B). No patients were identical to the consensus sequence.

The difference between the consensus sequences for HCV types 1a or 1b showed an overall amino acid sequence similarity of 96.4%. The conserved motifs were surprisingly similar differing by only 4 residues (259, 263, 269 & 270). No correlation could be made between mutations in HCV types 1a and 1b. Among all the sequences, amino acid substitutions at residues which are homologous in function to those of other helicases in the same family (shaded residues in the Tables 5A and 5B) were not found. However, several mutations were found within and in close proximity to the seven motifs. Most substitutions occur only in one sequence, suggesting a random substitution due to base misincorporation by RT polymerase. HCV1a sequences showed no substitutions in motif I, 1 substitution of L226I in motif Ia (pt. 4C), 1 substitution of S263G in the nucleic acid binding motif (pt. 4B), 1 V329I substitution in motif III (pt's. 23, 24, 270, 1H, 1X, 3T, 1C), 2 substitutions in motif IVa; K371R (pt. 1D) and K372R (pt's 4 and 1C), and 3 substitutions in motif V; A410S (1a control), A410T (pt. 3S) and F418Y (pt's. 4, 12, 177, 194, 198, 3P, 3S, 3T, 4C, K, and 174). The first gatekeeper motif had 1 substitution, S424T (pt's 1X and K), motif VI had 5 substitutions; R458S (pt. 3S), T459S (pt. 5P), R461L (pt. 3S), K469R (pt's. 1X, 5P, 174 and 183) and P470Q (pt. 4C), and the last gatekeeper motif had 3 substitutions; D496N (pt. 38), A497T (pt. 11) and G498S (pt. 4B). Of all the mutations, the substitutions in motif IVa were the most surprising since these two lysine residues, at positions 371 and 372, have been shown to be important in stabilizing the ss nucleic acid strand. The amino acid change of lysine to arginine in both cases indicates a need for a basic amino acid at this position. Another substitution which was interesting was at position 410 in motif V. This was interesting because the prototype sequence contained a serine instead of an alanine, a serine at this position is in most published sequences, however, the sequence presented herein identified as SEQ ID NO:1 showed an alanine presence in the patient derived consensus except for one patient who had an threonine at this position (pt. 3S). Positions 229, 418 and 469 proved interesting because several patients contained these substitutions, however, the significance of these remain unknown.

Amino acid substitutions in HCV1a isolates at positions outside existing motifs showed a high prevalence of mutations in several regions. A change from isoleucine to valine at position 248 occurred in 9 out of 30 HCV1a patients. Surrounding residues from 240 to 252 also showed a high degree of mutation. Residue 281 could be either glycine (consensus) or arginine (7 patients). This is surprising because the transition is from a simple to a bulky side chain. Other regions which contain higher frequency of substitution was from residue 229 to 358 and 382 to 386, residues 455 to 461, residue 557 and the COOH terminus.

Motif I in HCV1b sequences had 1 substitution, K213R (pt's. 3N and 3Q), no substitutions in Ia, 3 in the nucleic acid binding motif, A263G (control), P264S (control, pt's 1A, 2D, 3N, 6A) and I265V (pt. 3Q). Motif II had 2 substitutions; I288M (pt. 1U), and T295I (pt. 1A), motifs III and IVa did not contain any mutations, while motif V contained 2; V406A (pt. 30) and F418Y (pt. 3Q). Both gatekeeper motifs did not contain mutations. Motif VI contained 1 at position 470. This mutation was significant in that a total of 7 amino acids were found: R470S (control and pt. 6A), R470M (pt's. 1G, 1U and 3N), R470G (pt's 179 and 3Q), R470V (pt128), R470P (pt. 3O) and R470A (pt. 1). Similarities to HCV1a were found in regions outside of the known motifs. Positions 240 to 256, 334 to 358, 382 to 386 and the COOH terminus contained 'hot' regions.

The Effects of IFN Treatment.

The most significant differences were noticed when isolates were grouped according to whether or not the host had received interferon therapy. A significant overall decrease in sequence variability in both HCV types 1a and 1b was evident after IFN therapy with or without ribavirin. Thus, interferon plays a role in quasispecies selection.

For HCV1a isolates which had not been subjected to interferon therapy, the overall number of mutations per patient averaged 6.47 per sequence. A total of 59 different residues were affected. After interferon therapy, the number of mutations averaged 5.0 per patient with 25 sites containing different amino acids giving an overall 56.14% drop in positions mutated (Table 5A). For type 1b isolates, the average number of mutations per patient for isolates not subjected to interferon therapy was 8.9 with 53 sites varying overall. However, after interferon therapy, the number of mutations per patient was 6.33, and the number of sites which contained mutations dramatically dropped in the 1b isolates to only 16, or by 69.78% (Table 5B). This suggests that the sensitive strains were eliminated during interferon therapy and these remaining sites may somehow be involved in resistance of the virus to interferon. No differences in either type 1a or 1b were noticed for those isolates which were subjected to combination therapy with ribavirin as opposed to interferon alone, and no correlation could be made between number or positions of mutations and viral load.

All references cited herein are expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

TABLE 1A

| SEQ ID NO | HCV TYPE | NAME | SEQUENCE |
| --- | --- | --- | --- |
| 1 | 1a and 1b | 2539U | 5'-CCTGCTTGTGGATGATG-3' |
| 2 | | 5622L | 5'-CTGATGAAATTCCACATGTGCTTCGCCCA-3' |
| 3 | | 2727U | 5'-CTACTCCTGCTCCTGCTGGCGTT-3' |
| 4 | | 5442L | 5'-CACTCTTCCATCTCATCGAACTCCTGGTAGAG-3' |
| 5 | | 2916U | 5'-GTGTGGGTYCCCCCCCTCAAC-3' |
| 6 | | 5268L | 5'-GCCGACATGCATGYCATGATGTATTT-3' |
| 7 | | 3254U | 5'-GAGCCCGTCGTCTTCTC-3' |
| 8 | | 3486U | 5'-GGCCGGGACAASAACCA-3' |
| 9 | | 3723U | 5'-TCGGACCTTTACTTGGTCACGAG-3' |
| 10 | | 4240L | 5'-AGGAACTTGCCWTAGGTGGAGTA-3' |
| 11 | | 3753L | 5'-CGCCGGCGCACCGGAATGACATC-3' |
| 12 | | 4218U | 5'-TACTCCACCTATGGCAAGTTCCT-3' |
| 13 | | 4896U | 5'-GAGTGCTATGACGCGGGCTGTGCTT-3' |
| 14 | | 4284L | 5'-GAGTGGCACTCATCACA-3' |
| 15 | | 4509U | 5'-CATCTCATYTTCTGCCA-3' |
| 16 | | 4710L | 5'-TCGACTGTCTGRGTGACACA-3' |
| 17 | | 5145U | 5'-CCATCGTGGGAYCAAATGTGGAAGTGT-3' |
| 18 | | 5268U | 5'-AAATACATCATGRCATGCATGTCGGC-3' |
| 19 | | 5622U | 5'-TGGGCGAAGCACATGTGGAATTTCATCAG-3' |
| 20 | | 5993U | 5'-GCCATCCTCTCTCCTGGTGCCCT-3' |
| 21 | | 5790l | 5'-CACCCAYCCCCCCAAKATGTT-3' |
| 22 | | 3127U | 5'-CCGGRGGTCATTAYGTSCAAATGG-3' |
| 23 | | 5700L | 5'-CGCGGGGTTTCCAGGCAG-3' |

TABLE 1B

| SEQ ID NO | HCV TYPE | NAME | SEQUENCE |
| --- | --- | --- | --- |
| 24 | 2a | HCV2aU-1 | 5'-GGC ACY TAC ATC TAT GAY CA-3' |
| 25 | | HCV2aU-2 | 5'-TCA TCT TCA GTC CGA TGG AGA-3' |
| 26 | | HCV2aL-1 | 5'-ATG CCG CTR ATG AAR TTC CAC AT-3' |
| 27 | | HCV2aL-2 | 5'-CTG AAY GCC ATC ATG GAR GCC A-3' |

TABLE 1C

| SEQ ID NO | HCV TYPE | NAME | SEQUENCE |
| --- | --- | --- | --- |
| 28 | 2b | HCV2bU-1 | 5'-CCA ATG GAG AAG AAG GTC A-3' |
| 29 | | HCV2bU-2 | 5'-ATG TGG AGA CAT CCT GCA-3' |
| 30 | | HCV2bL-1 | 5'-TTG TGG CCT GTT GTA GGA-3' |
| 31 | | HCV2bL-2 | 5'-GCG CAT TCT TCC ATC TCA-3' |
| 32 | | HCV2b seqU1 | 5'-CCG AAA CGC TGA YGT CAT-3' |
| 33 | | HCV2b seqU2 | 5'-GGA TGG AGG CTG CTC AGC-3' |
| 34 | | HCV2b seqU3 | 5'-AGA CCC GAC CTT TAC CAT-3' |
| 35 | | HCV2b seqU4 | 5'-TTA CCC GTG TGT CAA GAC CA-3' |
| 36 | | HCV2b seqL1 | 5'-CCA ATG ATG GAR ATG CAG-3' |
| 37 | | HCV2b seqL2 | 5'-CCT TTG CSC TAG CGC ATA-3' |

TABLE 1C-continued

| SEQ ID NO | HCV TYPE | NAME | SEQUENCE |
|---|---|---|---|
| 38 | | HCV2b seqL3 | 5'-GAG CAC TAC GCT GTC GAA-3' |
| 39 | | HCV2b seqL4 | 5'-TGG CTG TGG CTA GAA CCA-3' |
| 40 | | HCV2b seqL5 | 5'-GTA GGC CCC AAA ACC AAG-3' |
| 41 | | HCV2b seqL6 | 5'-GCY CTG AAC AAG CCC ACG-3' |
| 42 | | HCV2b seqL7 | 5'-ACA TCT GRG TGA CTG GTC-3' |

TABLE 1D

| SEQ ID NO | HCV TYPE | NAME | SEQUENCE |
|---|---|---|---|
| 43 | 3a | HCV3aU-1 | 5'-CCY GTA ATA TTT AGT CCC A-3' |
| 44 | | HCV3aU-2 | 5'-TGG AAA TCA AGG TCA TCA-3' |
| 45 | | HCV3aL-1 | 5'-GTA GCT ACT ATG GGC TCA A-3' |
| 46 | | HCV3aL-2 | 5'-GCT TGC TCA TGT ACG GG-3' |

TABLE 1E

| SEQ ID NO | HCV TYPE | NAME | SEQUENCE |
|---|---|---|---|
| 47 | 3b | HCV3bU-1 | 5'-CCC GTC ATC TTT AGT CCT A-3' |
| 48 | | HCV3bU-2 | 5'-TGG AGA TTA AGG TTA TCA-3' |
| 49 | | HCV3bL-1 | 5'-GAT TGC ACT ATG GGT CGA A-3' |
| 50 | | HCV3bL-2 | 5'-GCT TGC TCG ATG TAA GGA-3' |

TABLE 1F

| SEQ ID NO | HCV TYPE | NAME | SEQUENCE |
|---|---|---|---|
| 51 | 4a | 3486U | 5'-GGC CGG GAC AAS AAC CA-3' |
| 52 | | 3723U | 5'-TCG GAC CTT TAC TTG GTC ACG AG-3' |
| 53 | | 3753L | 5'-CGC CGG CGC ACC GGA ATG ACA TC-3' |
| 54 | | 4218U | 5'-TAC TCC ACC TAT GGC AAG TTC CT-3' |
| 55 | | 4240L | 5'-AGG AAC TTG CCW TAG GTG GAG TA-3' |
| 56 | | 4284L | 5'-GAG TGG CAC TCA TCA CA-3' |
| 57 | | 4509U | 5'-CAT CTC ATY TTC TGC CA-3' |
| 58 | | 4710L | 5'-TCG ACT GTC TGR GTG ACA CA-3' |
| 59 | | 4896U | 5'-GAG TGC TAT GAC GCG GGC TGT GCT T-3' |
| 60 | | 5145U | 5'-CCA TCG TGG GAY CAA ATG TGG AAG TGT-3' |
| 61 | | 5268U | 5'-AAA TAC ATC ATG RCA TGC ATG TCG GC-3' |
| 62 | | 5268L | 5'-GCC GAC ATG CAT GYC ATG ATG TAT TT-3' |
| 63 | | 5442L | 5'-CAC TCT TCC ATC TCA TCG AAC TCC TGG TAG AG-3' |

TABLE 1G

| SEQ ID NO | BASE PAIRS | TYPE | SEQUENCE |
|---|---|---|---|
| 1 | −881 bp | Amplification | 5'-CCTGCTTGTGGATGATG-3' |
| 2 | 2230 bp | | 5'-CTGATGAAATTCCACATGTGCTTCGCCCA-3' |
| 3 | −693 bp | | 5'-CTACTCCTGCTCCTGCTGGCGTT-3' |
| 4 | 2053 bp | | 5'-CACTCTTCCATCTCATCGAACTCCTGGTAGAG-3' |
| 64 | −504 bp | | 5'-GTGTGGGTTCCCCCCCTCAACGT-3' |
| 6 | 1873 bp | | 5'-GCCGACATGCATGYCATGATGTATTT-3' |
| 7 | −166 bp | Sequencing | 5'-GAGCCCGTCGTCTTCTC-3' |
| 8 | 66 bp | | 5'-GGCCGGGACAASAACCA-3' |
| 9 | 303 bp | | 5'-TCGGACCTTTACTTGGTCACGAG-3' |
| 10 | 918 bp | | 5'-AGGAACTTGCCWTAGGTGGAGTA-3' |
| 11 | 355 bp | | 5'-CGCCGGCGCACCGGAATGACATC-3' |

TABLE 2

| A. NS3 Position | 30 | 33 | 48 | 63 | 105 | 118 | 126 | 213 | 234 | 238 | 264 | 271 | 291 | 357 | 372 | 453 | 457 | 495 | 527 | 540 |
|---|---|---|---|---|---|---|---|---|---|---|---|---|---|---|---|---|---|---|---|---|
| 1a pCV-H77C | G | A | T | G | C | A | C | C | G | C | T | T | A | T | G | C | A | G | A |
| 1a consensus | A | G | C | R | T | G | T | T | A | A | C | G | C | G | C | A | A | G | A | G |

| B. NS3 Position | 27 | 37 | 45 | 90 | 111 | 142 | 156 | 177 | 183 | 198 | 204 | 207 | 234 | 239 | 276 | 280 | 293 | 297 | 327 | 357 |
|---|---|---|---|---|---|---|---|---|---|---|---|---|---|---|---|---|---|---|---|---|
| 1b pCV-J4L6S | A | G | T | A | T | A | C | T | G | T | A | T | A | T | C | A | G | T | A | A |
| 1b consensus | G | C | C | G | C | T | C | A | C | G | C | R | A | T | T | C | C | G | G |

| B. NS3 Position | 372 | 375 | 403 | 408 | 414 | 427 | 432 | 438 | 449 | 450 | 457 | 471 | 489 | 507 | 508 | 531 | 534 | 543 |
|---|---|---|---|---|---|---|---|---|---|---|---|---|---|---|---|---|---|---|
| 1b pCV-J4L6S | A | T | C | A | C | T | T | T | T | C | G | T | C | C | A | T | C | T |
| 1b consensus | G | C | T | G | T | C | C | C | C | T | A | Y | T | T | G | C | T | C |

The nucleotide position within NS3 is indicated.

TABLE 3

```
              10          20          30          40          50          60
1a Con   APITAYAQQT  RGLLGCIITS  LTGRDKNQVE  GEVQIVSTAA  QTFLATCING  VCWTVYHGAG
1a       ----------  ----------  ----------  ---------T  ----------  ------●---
No Treatment
pt. K    ----------  ----------  ----------  ----------  ----------  ------●---
pt. 4    ----------  ----------  ----------  ----------  ----------  ------●---
pt. 12   ----------  ----------  --------A-  ----------  ----------  ------●---
pt. 24   ----------  ----------  ----------  ----------  ----------  ------●---
pt. 161  ----------  ----------  ----------  ----------  ----------  ------●---
pt. 170  ----------  ----------  --------A-  ----------  ----------  ------●---
pt. 177  ----------  ----------  --------A-  ----------  ----------  ------●---
pt. 194  ----------  ----------  ----------  ----------  ----------  ------●---
pt. 1C   ----------  ----------  ----------  ---------T  ----------  ------●---
pt. 1H   ----------  ----------  ----------  ---------T  ----------  ------●---
pt. 1X   ------T---  ----------  ----------  ----------  ----------  ------●---
IFC Treatment
pt. 11   ----------  ----------  ----------  --------A-  ----------  ------●---
pt. 252  ----------  ----------  ----------  --I-V-----  -S--------  ------●---
pt. 174  ----------  ----------  ------D---  ----------  ----------  ------●---
pt. 176  ----------  ----------  ----------  ----------  ----------  ------●---
pt. 183  ----------  ----------  -----N----  ----------  ----------  ------●---
pt. 186  ----------  ----------  ----------  ----------  ----------  ------●---
pt. 1D   ----------  ----------  ----------  ----------  ----------  ------●---
pt. 1Y   ----------  ----------  ----------  ----------  ----------  ------●---
1a amb.  ------*---  ----------  -----**-*-  --*-*----*  -*--------  ------●---
```

```
              70          80          90         100         110         120
1a Con   TRTIASPKGP  VIQMYTNVDK  DLVGWPAPQG  ARSLTPCTCG  SSDLYLVTRH  ADVIPVRRRG
1a       ----------  ---------Q  ●---------  S-----●-●-  ----------  ----------
No Treatment
pt. K    ----------  ----------  ●---------  S-----●-●-  ----------  ----------
pt. 4    ----------  ----------  ●---------  ------●-●-  ----------  ----------
pt. 12   ------S---  ----------  ●---------  T-----●-●-  ----------  ----------
pt. 24   ---M------  ----------  ●---------  ------●-●-  ----------  ----------
pt. 161  ----------  ----------  ●---------  ------●-●-  ----------  ----------
pt. 170  ----------  ----------  ●---------  T-----●-●-  ----------  ----------
pt. 177  ----------  ----------  ●---------  T-----●-●-  ----------  ----------
pt. 194  ----------  ---------Q  ●---------  ------●-●-  ----------  ----------
pt. 1C   ----------  ----------  ●---------  ------●-●-  ----------  ----------
pt. 1H   ----------  ----------  ●---------  T-----●A●-  ----------  --------Q-
pt. 1X   ----------  ----------  ●---------  ------●-●-  ----------  --------Q-
IFC Treatment
pt. 11   ----------  ----------  ●---------  T-----●-●-  ----------  ----------
pt. 252  S---------  ----------  ●---------  S-----●-●-  ----------  ----------
pt. 174  ----------  ----------  ●---------  S-----●-●-  ----------  ----------
pt. 176  ----------  ---------Q  ●---------  ------●-●-  ----------  ----------
pt. 183  A---------  ----------  ●----L----  ------●-●-  ----------  ----------
pt. 186  ----------  ----------  ●---------  ------●-●-  ----------  --------Q-
pt. 1D   ---L------  I---------  ●----S----  ------●-●-  ----------  ----------
pt. 1Y   ----------  ----------  ●---------  S-----●-●-  ----------  ----------
1a amb.  **-*--*---  *--------*  ●----*----  *-----●*●-  ----------  --------*-
```

TABLE 3-continued

```
             130        140        150        160        170        180
ia Con       DSRGSLLSPR PISYLKGSSG GPLLCPAGHA VGIFRAAVCT RGVAKAVDFI PVENLETTMR S
1a           ---------- --------●- ----●---●- --L------- ---------- -----G---- -
No Treatment
pt. K        ---------- --------●- ----●---●- ---------- ---------- ---------- -
pt. 4        ---------- --------●- ----●---●- ---------- ---------- ---------- -
pt. 12       ---------- --------●- ----●---●- ---------- ---------- ---------- -
pt. 24       ---------- --------●- ----●---●- ---------- ---------- ---------- - pt. 161      ---------- --------●- ----●---●- ---------- ---------- ---------- -
pt. 170      ---------- --------●- ----●---●- ---------- ---------- ---------- -
pt. 177      ---------- --------●- ----●---●- ---------- ---------- ---------- -
pt. 194      ---------- --------●- ----●---●- --L------- ---------- ---------- -
pt. 1C       ----G----- --------●- ----●---●- ---------- ---------- ---------- -
pt. 1H       ---------- --------●- ----●---●- ---------- ---------- ---------- -
pt. 1X       ---------- -V------●- ----●---●- ---------- ---------- ---------- -

IFN Treatment
pt. 11       ---------- --------●- ----●---●- ---------- ---------- ---------- -
pt. 252      ---------- --------●- ----●---●- ---------- ---------- ---------- -
pt. 174      ---------- --------●- ----●---●- ---------- ---------- ---------- -
pt. 176      ---------- --------●- ----●---●- ---------- ---------- ---------- -
pt. 183      ---------- --------●- ----●---●- ---------- ---------- ---------- - pt. 186      ---------- --------●- ----●---●- ---------- ---------- ---------- -
pt. 1D       ---------- --------●- ----●---●- --L------- ---------- ---------- -
pt. 1Y       ---------- --------●- ----●---●- ---------- ---------- ---------- -
1a amb.      ----*----- -*------●- ----●---●- --*------- ---*-*---- ---------- -
```

TABLE 4

```
               10         20         30         40         50         60         70         80         90        100
1b Con APITAYSQQT RGLLGCIITS LTGRDKNQVE GEVQVVSTAT QSFLATCVNG VCWTVHGAG SKTLAGPKGP ITQMYTNVDQ DLVGWQAPPG ARSLTPCTCG
1b     ---------- ---V------ ---------- ---------- ---------- ---------- ---------- ---------- ---------- --M--S----
No Treatment
pt. 1    ---------- ---------- ---------- ---------- ---------- ---●------ ---------- ---------- ●●●●●●●●●● ●●●●●●●●●●
pt. 153  ---------- ---------- ---------- ---------- ----I----- ---●------ ---------- ---------- ●●●●●●●●●● ●●●●●●●●●●
pt. 1A   ----F----- ---------- ---------- ---------- ---------- ---●---C-- ---------- ---------- ●●●●●●●●●● ●●●●●●●●●●
pt. 1G   ---A-F---- ---------- ---------- ---------- ----I----- --S●------ -------Q-- ---------- ●●●●●●●●●● ●●●●●●●●●●
pt. 1U   ---A------ ---------- ---------- ---------- ----I----- --F●------ -------A-- ---------- ●●●●●●●●●● ●●●●●●●●●●
pt. 2D   ---------- ---------- ---------- ---------- ---------- ---●------ ---T------ ---------- ●●●●●●●●●● ●●●●●●●●●●
pt. 2F   ---------- ---------- ---------- ---------- ---------- ---------- ---------- ------S--- ---------- ----------
pt. 23   ---------- ---------- ---------- ---------- ---------- ---●---K-- ---------- ---Q------ ●●●●●●●●●● ●●●●●●●●●●
IFN Treatment
pt. 179  ---------- ---------- ---------- ---------- ---------- ---●------ -T-----V-- ---------- ●●●●●●●●●● ●●●●●●●I●●
pt. 205  ---------- ---------- ---------- ---------- ---------- ---●------ -T-S------ ---------- ●●●●●●●●●● ●●●●●●●●●●
pt. 25   ---------- ---------- ---------- ---------- ---------- ---●------ ---L------ ---Q-V---- ●●●●●●●●●● ●●●●●●●●●●
1b amb.  ------*-** ---------- ---------- ---------- ---------* ---*---*-- ***-*-*--* ---*--*--* ●●●●●●●●●● ●●●●●●**●●

110          120          130          140          150          160         170          180
1b Con    SSDLYLVTRH ADVIPVRRRG DSRGSLLSPR PVSYLKGSSG GPLLCPSGHA VGIFRAAVCT RGVAKAVDFV PVESMETTMR S
1b        ---------- ---------- ---------- ---------- ---------- ---------- ---------I ---------- -
No Treatment
pt. 1     ---------- ---------- ---------- ---------I ●●●●●●●●●● ●-V------- ---------- ---------- -
pt. 153   ---------- ---------- ---------- ---------- ●●●●●●●●●● ●●●------- ---------- ---------- -
pt. 1A    ---------- ---------- ---------- ---------I ●●●●●●●●●● ●●●------- ---------- ---------- -
pt. 1G    ---Q------ ---------- -------C-- ---------- ●●●●●●●●●● ●●●------- ---------- ---------- -
pt. 1U    ---------- ---------- ---------- ---------I ●●●●●●●●●● ●●●------- ---------- ---------I -
pt. 2D    ---------- ---------- ---------- ---------- ---------- ---------- ---------- ---------- -
pt. 2F    ---------- ---------- ------L--- ---------I ●●●●●●●●●● ●●●------- ---------- ---------- -
pt. 23    ---------- ---------- ---------- ---------- ●●●●●●●●●● ●●●------- ---------- ---------- -
IFN Treatment
pt. 179   ---------- ---------- ---------- ---------- ●●●●●●●●●● ●●●------- ---------- --------S- -
pt. 205   ---------- ---------- ---------- ---------I ●●●●●●●●●● ●●●------- ---------I ---------- -
pt. 25    ---------- ---------- ---------- ---------- ●●●●●●●●●● ●●●------- ---------- --------S- -
1b amb.   ---------* ---------- ---------- ---------* ●●●●●●●●●● ●●●-----*- ---------* ---*----*- *
```

TABLE 5A

| | 190 | 200 | 210 | 220 | 230 | 240 | 250 | 260 | 270 | 280 |
|---|---|---|---|---|---|---|---|---|---|---|
| Consensus | PVFTDNSSP | PAVPQSFQVA | HLHAPTGSGK | STKVPAAYAA | QGYKVLVLNP | SVAATLGFGA | YMSKAHGIDP | NIRTGVRTIT | TGSPITYSTY | GKFLADGGCS |
| 1a | --------- | ---------- | ---------- | ---------- | ---------- | ---------- | ----V----- | ---------- | ---------- | ---------- |
| No Treatment | | | | | | | | | | |
| pt. 4 | --------- | ---------- | ---------- | ---------- | ---------- | ----o----- | ---------- | ---------- | ----o----- | ---------- |
| pt. 12 | --------- | ---------- | ---------- | ---------- | ---------- | ----o----- | ----E----- | ---------- | ----o----- | ---------- |
| pt. 23 | --------- | ----T----- | ---------- | ---------- | ---------- | ----o----- | ---------- | ---------- | ----o----- | ---------- |
| pt. 24 | --------- | ---------- | ---------- | ---------- | ---------- | ----o----- | ---------- | ---------- | ----o----- | ---------- |
| pt. 170 | --------- | ---------- | ---------- | ---------- | ---------- | ----o----- | ---------- | ---------- | ----o----- | ---------- |
| pt. 177 | --------- | ---------- | ---------- | ---------- | ---------- | ----o----- | ---------- | ---------- | ----o----- | ---------- |
| pt. 194 | --------- | ---------- | ---------- | ---------- | ---------- | ----o----- | ----V----- | ---------- | ----o----- | ---------- |
| pt. 198 | --------- | ---------- | ---------- | ---------- | ---------- | ----o----- | ----E----- | ---------- | ----o----- | ---------- |
| pt. 1H | --------- | ---------- | ---------- | ---------- | ---------- | ----o----- | ----V-V--- | ---------- | ----o----- | ---------- |
| pt. 1X | --------- | ---------- | ---------- | ---------- | ---------- | ----o----- | ----V----- | ---------- | ----o----- | ---------- |
| pt. 3P | --------- | ---------- | ---------- | ---------- | ---------- | ----o----- | ---------- | ----V----- | ----o----- | ---------- |
| pt. 3S | ----T---- | ---------- | ---------- | ---------- | ---------- | ----o----- | ----V----- | ---------- | ----o----- | ---------- |
| pt. 3T | --------- | ---------- | ---------- | ---------- | ---------- | ----o----- | ---------- | ---------- | ----o----- | ---------- |
| pt. 4B | --------- | ---------- | ---------- | ---------- | ----I----- | ----o----- | ---------- | ---------- | ----o----- | ---------- |
| pt. 4C | ----V---- | ---------- | ---------- | ---------- | ---------- | ----o----- | ---------- | ---------- | ----o----- | ---------- |
| pt. 4V | --------- | ---------- | ---------- | ---------- | ---------- | ----o----- | ---------- | ----G----- | ----o----- | ---------- |
| pt. 5P | --------- | ---------- | ---------- | ---------- | ---------- | ----o----- | ----R----- | ---------- | ----o----- | ---------- |
| pt. 5Y | --------- | ---------- | ---------- | ---------- | ---------- | ----o----- | ---------- | ---------- | ----o----- | ----S----- |
| pt. 5Z | --------- | ---------- | ---------- | ---------- | ---------- | ----o----- | ---------- | ---------- | ----o----- | ---------- |
| IFN Treatment | | | | | | | | | | |
| pt. K | --------- | ---------- | ---------- | ---------- | ---------- | ----V----- | ----V----- | ---------- | ----o----- | ---------- |
| pt. 11 | --------- | ---------- | ---------- | ---------- | ---------- | ----o----- | ---------- | ---------- | ----o----- | ---------- |
| pt. 25 | --------- | ---------- | ---------- | ---------- | ---------- | ----o----- | ----V----- | ---------- | ----o----- | ---------- |
| pt. 161 | --------- | ---------- | ---------- | ---------- | ---------- | ----o----- | ---------- | ---------- | ----o----- | ---------- |
| pt. 174 | --------- | ---------- | ---------- | ---------- | ---------- | ----o----- | ----V----- | ---------- | ----o----- | ---------- |
| pt. 176 | --------- | ---------- | ---------- | ---------- | ---------- | ----o----- | ---------- | ----L----- | ----o----- | ---------- |
| pt. 183 | --------- | ---------- | ---------- | ---------- | ---------- | ----o----- | ---------- | ---------- | ----o----- | ---------- |
| pt. 186 | --------- | ---------- | ---------- | ---------- | ---------- | ----o----- | ----V----- | ---------- | ----o----- | ---------- |
| pt. 252 | --------- | ---------- | ---------- | ---------- | ---------- | ----o----- | ---------- | ---------- | ----o----- | ---------- |
| pt. 1C | --------- | ---------- | ---------- | ---------- | ---------- | ----o----- | ----V----- | ---------- | ----o----- | ---------- |
| pt. 1D | --------- | ---------- | ---------- | ---------- | ---------- | ----o----- | ---------- | ---------- | ----o----- | ---------- |
| 1a amb. | ----*---- | ----*----- | ---------- | ---------- | ----*----- | ----*----- | ----*-***- | ----*----- | ----*----- | ----*----- |
| Impt. A.A. | | | ●●●●●●● | ●●● | ●●●●●●● | ●●●●●●●● | | | ●●●●●●●● | ●●●●● |
| | | | Motif I | | Motif Ia | | | | Nucleic Acid Binding | |

TABLE 5A-continued

|  | 290 | 300 | 310 | 320 | 330 | 340 | 350 | 360 | 370 | 380 |
|---|---|---|---|---|---|---|---|---|---|---|
| Consensus | GGAYDIIICD | ECHSTDATSI | LGIGTVLDQA | ETAGARLVVL | ATATPPGSVT | VPHPNIEEVA | LSTTGEIPFY | GKAIPLEVIK | GGRHLIFCHS | KKKCDELAAK |
| 1a | ---------- | ---------- | ---------- | ---------- | ---------- | ---------- | ---------- | ---------- | ---------- | ---------- |
| *No Treatment* | | | | | | | | | | |
| pt. 4 | ---------- | ---------- | ---------- | ---------- | ---------- | -S-------- | ---------- | ---------- | ----●----- | --R-----T- |
| pt. 12 | ---------- | ---------- | ---------- | ---------- | ---------- | ---------- | ---------- | ---------- | ----●----- | --------T- |
| pt. 23 | ---------- | ---------- | ---------- | ---------- | ---------- | ---------- | ---------- | ---------- | ----●----- | ---------- |
| pt. 24 | ---------- | ---------- | ---------- | ---------- | ----I----- | ---------- | ---------- | ---------- | ----●----- | ---------- |
| pt. 170 | ---------- | ---------- | ---------- | ---------- | ----I----- | --H------- | ---------- | ---------- | ----●----- | ---------- |
| pt. 177 | ---------- | ---------- | ---------- | ---------- | ----I----- | ---------- | ---------- | ---------- | ----●----- | ---------- |
| pt. 194 | ---------- | ----V----- | ---------- | ---------- | ---------- | ---------- | ---------- | ---------- | ----●----- | ---------- |
| pt. 198 | R--------- | ---------- | ---------- | ---------- | ---------- | ---------- | ---------- | ---------- | ----●----- | ---------- |
| pt. 1H | ---------- | ---------- | ---------- | ---------- | ----I----- | -S-------- | ---------- | ---------- | ----●----- | ---------- |
| pt. 1X | ---------- | ---------- | ---------- | ---------- | ----I----- | ---------- | ---------- | -------A-- | ----●----- | -----V-T- |
| pt. 3P | R--------- | ---------- | ---------- | ---------- | ---------- | -S-------- | ---------- | ---------- | ----●----- | ---------- |
| pt. 3S | R--------- | ---------- | ----T----- | ---------- | ---------- | ---------- | ---------- | ---------- | ----●----- | ---------- |
| pt. 3T | R--------- | ---------- | ---------- | ---------- | ----I----- | ---------- | -----A---- | ---------- | ----●----- | ---------- |
| pt. 4B | R--------- | ---------- | ---------- | ---------- | ---------- | ---------- | ---------- | ---------- | ----●----- | ---------- |
| pt. 4C | ---------- | ---------- | ---------- | ---------- | ---------- | --A------- | ---------- | -------V-- | ----●----- | ---------- |
| pt. 4V | ---------- | ---------- | ---------- | ---------- | ---------- | ---------- | -------V-- | ---------- | ----●----- | ---------- |
| pt. 5P | R--------- | ---------- | ---------- | ---------- | ---------- | ----*----- | ---------- | ---------- | ----●----- | ---------- |
| pt. 5Y | ---------- | ---------- | ---------- | ---------- | ---------- | ---------- | ---------- | -------A-- | ----●----- | ---------- |
| pt. 5Z | ---------- | ---------- | ---------- | ---------- | ---------- | ---------- | ---------- | ---------- | ----●----- | ---------- |
| *IFN Treatment* | | | | | | | | | | |
| pt. K | ---------- | ---------- | ---------- | ---------- | ---------- | -S-------- | ---------- | -------A-- | ----●----- | ---------- |
| pt. 11 | ---------- | ---------- | ---------- | ---------- | ---------- | -S-------- | ---------- | ---------- | ----●----- | ---------- |
| pt. 25 | ---------- | ---------- | ---------- | ---------- | ---------- | ---------- | ---------- | -------A-- | ----●----- | ---------- |
| pt. 161 | ---------- | ---------- | ---------- | ---------- | ---------- | ---------- | ---------- | ---------- | ----●----- | ---------- |
| pt. 174 | ---------- | ---------- | ---------- | ---------- | ---------- | ---------- | ---------- | -------A-- | ----●----- | ---------- |
| pt. 176 | ---------- | ---------- | ---------- | ---------- | ---------- | ---------- | ---------- | ---------- | ----●----- | ---------- |
| pt. 183 | ---------- | ---------- | ---------- | ---------- | ---------- | ----G----- | -------V-- | ---------- | ----●----- | ---------- |
| pt. 186 | ---------- | ---------- | ---------- | ---------- | ---------- | ---------- | ---------- | -------A-- | ----●----- | ---------- |
| pt. 252 | ---------- | ---------- | ---------- | ---------- | ---------- | ---------- | ---------- | ---------- | ----●----- | ---------- |
| pt. 1C | ---------- | ---------- | ---------- | ---------- | ----I----- | ---------- | ---------- | ---------- | ----●----- | --R------- |
| pt. 1D | R--------- | ---------- | ---------- | ---------- | ---------- | ---------- | ---------- | -------*-- | ----●----- | --R------- |
| 1a amb. | *--------- | ----*----- | --------*- | ---------- | ----*----- | ----*----- | -*---*---- | -*-----*-- | **●----- | ------** |
| Impt. A.A. | ---------●●●●● | ---------- | ---------- | ●●●●●●●●●● | ●●●●----- | ---------- | ---------- | ---------- | ●●●●●----- | ---------- |
|  | Motif II | | | Motif III | | | | | Motif IVa | |

TABLE 5A-continued

| | 390<br>LVALGINAVA | 400<br>YYRGLDVSVI | PTSGDVVVVA | 410<br>TDALMTGFTG | DFDSVIDCNT | 420 | 430<br>CVTQTVDFSL | DPTFTIETTT | 440<br>LPQDAVSRTQ | 450<br>RRGRTGRKP | 460<br>GIYRFVAPGE | 470 | 480 |
|---|---|---|---|---|---|---|---|---|---|---|---|---|---|
| Consensus 1a | | | | | | | | | | | | | |
| No Treatment | | | | | | | | | | | | | |
| pt. 4 | --------- | --------- | ------S-- | --------- | --------- | --------- | --------- | --------- | --------- | --------- | --------- | ---T----- | |
| pt. 12 | -T------- | --------- | --------- | o-------- | --Y------ | --------- | --------- | --------- | --------- | --------- | --------- | ---T----- | |
| pt. 23 | --------- | --------- | --------- | o-------- | --Y------ | --------- | --------- | --------- | --------- | --------- | --------- | --------- | |
| pt. 24 | --M------ | --------- | --------- | o-------- | --------- | --------- | --------- | --------- | --------- | --------- | --------- | --------- | |
| pt. 170 | -S--V---- | --------- | --------- | o-------- | --Y------ | --------- | --------- | --------- | --------- | --------- | --------- | --------- | |
| pt. 177 | ---V----- | --------- | --------- | o-------- | --Y------ | --------- | --------- | --------- | --------- | --------- | --------- | --------- | |
| pt. 194 | -G--V---- | --------- | --------- | o-------- | --Y------ | --------- | --------- | --------- | --------- | --------- | --------- | --------- | |
| pt. 198 | -S--V---- | --------- | --------- | o-------- | --------- | --------- | --------- | --------- | --------- | --------- | --------- | --------- | |
| pt. 1H | --M-V---- | --------- | --------- | o-------- | --Y------ | --------- | -T------- | --------- | ------C-- | --------- | --------- | ---R----- | |
| pt. 1X | --------- | --------- | --------- | o-------- | --------- | --------- | --------- | --------- | --------- | --------- | --------- | --------- | |
| pt. 3P | --------- | --------- | ----T---- | o-------- | --Y------ | --------- | --------- | --------- | --S--S--- | --------- | --------- | --------- | |
| pt. 3S | --------- | --------- | --------- | o-------- | --Y------ | --------- | ---D----- | --------- | --------- | --L------ | --------- | --------- | |
| pt. 3T | --------- | --------- | --------- | o-------- | --------- | --------- | --------- | --------- | --------- | --------- | --------- | --------- | |
| pt. 4B | --------- | --------- | --------- | o-------- | --Y------ | --------- | --------- | --------- | --------- | --------- | --------- | --------- | |
| pt. 4C | ---V----- | --------- | --------- | o-------- | --------- | --------- | ---D----- | --------- | --------- | --------- | --------- | ---Q----- | ---T----- |
| pt. 4V | ---V----- | --------- | --------- | o-------- | --------- | --------- | --------- | --------- | --------- | --------- | --------- | --------- | |
| pt. 5P | --------- | --------- | --------- | o-------- | --------- | --------- | --------- | --------- | --------- | --------- | --------- | --------- | |
| pt. 5Y | -G------- | --------- | --------- | o-------- | --------- | --------- | --------- | --------- | --------- | --S------ | --------- | ---R----- | ---T----- |
| pt. 5Z | -T------- | ------I-- | --------- | o-------- | --------- | --------- | --------- | --------- | --------- | --------- | --------- | --------- | |
| IFN Treatment | | | | | | | | | | | | | |
| pt. K | --------- | --------- | --------- | --------- | --------- | --------- | --------- | --------- | --------- | --------- | --------- | --------- | |
| pt. 11 | -T------- | --------- | --------- | --------- | --------- | --------- | --------- | --------- | --------- | --------- | --------- | --------- | |
| pt. 25 | ---V----- | --------- | --------- | --------- | --------- | --------- | --------- | --------- | --------- | --------- | --------- | --------- | |
| pt. 161 | ---V----- | --------- | --------- | --------- | --------- | --------- | --------- | --------- | --------- | --------- | --------- | --------- | |
| pt. 174 | ---V----- | --AN----- | --------- | --------- | --Y------ | --------- | --------- | --------- | --------- | --------- | --------- | ---R----- | ---T----- |
| pt. 176 | --------- | ------S-- | --------- | --------- | --------- | --------- | --------- | --------- | --------- | --------- | --------- | --------- | |
| pt. 183 | ---V----- | --------- | --------- | --------- | --------- | --------- | -T------- | --------- | --------- | --------- | --------- | --------- | |
| pt. 186 | --------- | --------- | --------- | --------- | --------- | --------- | --------- | --------- | --------- | --------- | --------- | --------- | |
| pt. 252 | -G--V---- | --------- | --------- | --------- | --------- | --------- | --------- | --------- | --------- | --------- | --------- | ---R----- | ---T----- |
| pt. 1C | -G--V---- | --------- | --------- | --------- | --------- | --------- | --------- | --------- | --------- | --------- | --------- | --------- | |
| pt. 1D | -G--L---- | --------- | --------- | --------- | --------- | --------- | --------- | --------- | --------- | --------- | --------- | --------- | |
| 1a amb. | -***--- | --------- | ------- | -*------- | --*------ | --------- | -*------- | --------- | --*------ | -***--- | --------- | ------- | ---*----- |
| Impt. A.A. | --------- | --------- | ●●●●●●●●● | ●●●●●●●●● | --------- | --------- | ●●●●●●●●●● | --------- | --------- | --------- | ●●●●●●●●● | | |
| | | | Motif V | | Gatekeeper | | | | | | Motif VI | | |

TABLE 5A-continued

| | 490 | 500 | 510 | 520 | 530 | 540 | 550 | 560 | 570 | 580 |
|---|---|---|---|---|---|---|---|---|---|---|
| Consensus 1a | RPSGMFDSSV | LCECYDAGCA | WYELTPAETT | VRLRAYMNTP | GLPVCQDHLE | FWEGVFTGLT | HIDAHFLSQT | KQSGENLPYL | VAYQATVCAR | AQAPPPSWDQ |
| No Treatment | | | | | | | | | | |
| pt. 4 | ---------- | ---------- | -----o---- | ---------- | ---------- | ---------- | ---------- | -----F---- | ---------- | ---------- |
| pt. 12 | ---------- | ---------- | ------o--- | ---------- | ---------- | ---------- | ---------- | ---------- | ---------- | ---------- |
| pt. 23 | -------I-- | ---------- | ------o--- | ---------- | ---------- | ---------- | ---------- | ---------- | ---------- | ---------- |
| pt. 24 | -------I-- | ---------- | ------o--- | ---------- | ---------- | ---------- | ---------- | ---------- | ---------- | ---------- |
| pt. 170 | ---------- | ---------- | ------o--- | ---------- | ---------- | ---------- | ---------- | ---------- | ---------- | ---------- |
| pt. 177 | ---------- | ---------- | ------o--- | ---------- | ---------- | ---------- | ---------- | -----F---- | ---------- | ---------- |
| pt. 194 | ---------- | ---------- | ------o--- | ---------- | ---------- | ---------- | -M-------- | -----F---- | ---------- | ---------- |
| pt. 198 | ---------- | ---------- | ------o--- | ---------- | ---------- | ---------- | ---------- | ---------- | ---------- | ---------- |
| pt. 1H | -------I-- | ---------- | ------o--- | ---------- | ---------- | ---------- | ---------- | -----F---- | ---------- | ---------- |
| pt. 1X | ---------- | ---------- | ------o--- | ---------- | ---------- | ---------- | ---------- | ---------- | ---------- | ---------- |
| pt. 3P | ---------- | -Q-N------ | ------o--- | ---------- | ---------- | ---------- | ---------- | -----F---- | ---------- | ---------- |
| pt. 3S | ---------- | ---S------ | ------o--- | ---------- | ---------- | ------A--- | ---------- | ---------- | ---------- | ---------- |
| pt. 3T | ---------- | ---------- | ------o--- | ---------- | ---------- | ---------- | ---------- | ---------- | ---------- | ---------- |
| pt. 4B | ---------- | ---------- | ------o--- | ---------- | ---------- | ---------- | ---------- | ---------- | ---------- | ---------- |
| pt. 4C | ----L----- | ---------- | ------o--- | ---------- | ---------- | ---------- | ---------- | ---------- | ---------- | ---------- |
| pt. 4V | ---------- | ---------- | ------o--- | ---------- | ---------- | ---------- | ---------- | -----F---- | -------D-- | ---------- |
| pt. 5P | ---------- | ---------- | ------o--- | ---------- | ---------- | ---------- | ---------- | -----F---- | ---------- | ---------- |
| pt. 5Y | ---------- | ---------- | ------o--- | ---------- | ---------- | ---------- | ---------- | --------I- | ---------- | ---------- |
| pt. 5Z | ---------- | ---------- | ------o--- | ---------- | ---------- | ---------- | ---------- | ---------- | ---------- | ---------- |
| IFN Treatment | | | | | | | | | | |
| pt. K | ---------- | ---------- | ------o--- | ---------- | ---------- | ---------- | ---------- | ---------- | ---------- | ---------- |
| pt. 11 | ---------- | ---T------ | ------o--- | ---------- | ---------- | ---------- | ---------- | ---------- | ---------- | ---------- |
| pt. 25 | ---------- | ---------- | ------o--- | ---------- | ---------- | ---------- | ---------- | -----F---- | ---------- | ---------- |
| pt. 161 | ---------- | ---------- | ------o--- | ---------- | ---------- | ---------- | ---------- | ---------- | ---------- | ---------- |
| pt. 174 | ---------- | ---------- | ------o--- | ---------- | ---------- | ---------- | ---------- | ---------- | ---------- | ---------- |
| pt. 176 | ---------- | ---------- | ------o--- | ---------- | ---------- | ---------- | ---------- | -----F---- | ---------- | ---------- |
| pt. 183 | ---------- | ---------- | ------o--- | ---------- | ---------- | ---------- | ---------- | -----F---- | ---------- | ---------- |
| pt. 186 | ---------- | ---------- | ------o--- | ---------- | ---------- | ---------- | ---------- | ---------- | ---------- | ---------- |
| pt. 252 | ---------- | ---------- | ------o--- | ---------- | ---------- | ---------- | ---------- | ---------- | ---------- | ---------- |
| pt. 1C | ---------- | ---------- | ------o--- | ---------- | ---------- | ---------- | ---------- | -----F---- | ---------- | ---------- |
| pt. 1D | ---------- | ---------- | ------o--- | ---------- | ---------- | ---------- | ---------- | -----F-*-- | ---------- | ---------- |
| 1a amb. | --*----*-* | -*-****--- | ------o--- | ---------- | ---------- | ---------- | ---------* | --------*- | ------*--- | ---------- |
| Impt. A.A. | | ●●●● ●●●●● | | | | | | | | |
| | | Gatekeeper | | | | | | | | |

TABLE 5A-continued

|  | 590 | 600 | 610 | 620 | 630 |
|---|---|---|---|---|---|
| Consensus | MWKCLIRLKP | TLHGPTPLLY | RLGAVQNEVT | LTHPVTKYIM | TCMSADLEVV T |
| 1a | ---------- | ---------- | ---------- | ----I----- | ---------- - |
| No Treatment | | | | | |
| pt. 4 | ---------- | ---------- | ---------- | ---------- | ---------- - |
| pt. 12 | ---------- | ---------- | ---------- | ----I----- | ----A----- - |
| pt. 23 | ----T----- | ---------- | ---------- | ---------- | ---------- - |
| pt. 24 | ----T----- | ---------- | ---------- | ----I----- | ---------- - |
| pt. 170 | ----T----- | ---------- | -------I-- | ---------- | ---------- - |
| pt. 177 | ---------- | ---------- | ---------- | ----I----- | ---------- - |
| pt. 194 | ----T----- | ---------- | ---------- | ----I----- | ---------- - |
| pt. 198 | ---------- | ---------- | ---------- | ----I----- | ---------- - |
| pt. 1H | ---------- | ---------- | ---------- | ---------- | ---------- - |
| pt. 1X | ---------- | N--------- | ---------- | ---------- | ---------- - |
| pt. 3P | ---------- | ---------- | --------I- | ----I----- | ----A----- - |
| pt. 3S | ---------- | ---------- | ---------- | ----I----- | ---------- - |
| pt. 3T | ---------- | ---------- | ---------- | ---------- | ---------- - |
| pt. 4B | ---------- | ---------- | ---------- | ----I----- | ---------- - |
| pt. 4C | ---------- | ---------- | ---------- | ----I----- | ---------- - |
| pt. 4V | ---------- | ---------- | ---------- | ---------- | ---------- - |
| pt. 5P | ---------- | ---------- | -------I-- | ----I----- | ---------- - |
| pt. 5Y | ---------- | ---------- | ---------- | ----I----- | ---------- - |
| pt. 5Z | ---------- | ---------- | ---------- | ---------- | ---------- - |
| IFN Treatment | | | | | |
| pt. K | ----T----- | ---------- | ---------- | ----I----- | ----A----- - |
| pt. 11 | ---------- | ---------- | ---------- | ---------- | ---------- - |
| pt. 25 | ---------- | ---------- | -------I-- | ---------- | ---------- - |
| pt. 161 | ----T----- | ---------- | ---------- | ----I----- | ---------- - |
| pt. 174 | ---------- | ---------- | ---------- | ----I----- | ----A----- - |
| pt. 176 | ---------- | ---------- | ---------- | ----I----- | ---------- - |
| pt. 183 | ---------- | ---------- | ---------- | ---------- | ---------- - |
| pt. 186 | ---------- | ---------- | ---------- | ---------- | ---------- - |
| pt. 252 | ----T----- | ---------- | ---------- | ---------- | ---------- - |
| pt. 1C | ----T----- | ---------- | ---------- | ---------- | ---------- - |
| pt. 1D | ---------- | ---------- | --------I- | ---------- | ---------- - |
| 1a amb. | ----*----- | ----*----- | --**---*-* | ----*----- | ----*----- - |
| Impt. A.A. | ---------- | ---------- | ---------- | ---------- | ---------- - |

\* = T/A

TABLE 5B

```
                  190        200        210        220        230        240        250        260
Consensus     PVFTDNSSP  PAVPQTFQVA HLHAPTGSGK STKVPAAYAA QGYKVLVLNP SVAATLGFGA YMSKAHGVDP NIRTGVRTIT
1b            -------T-  ---------- ---------- ---------- ---------- o--------- -------I-- ----------
No Treatment
pt. 128       ---------  ---------- ---------- ---------- ---------- o-------P- ---------- ----------
pt. 1A        ---------  ---------- ---------- ---------- ---------- o--------- ---------- ----------
pt. 1G        ---------  ---------- ---------- ---------- ---------- o--------V -----Y---- ----------
pt. 1U        ---------  ---------- ---------- ---------- ---------- o--------- ---------- ----------
pt. 2D        ---------  ---------- -----S---- ---------- ---------- o--------- ---------- ----------
pt. 2F        ---------  ---------- ---------- ---------- ---------- o--------- ---------- ---S------
pt. 3N        ---------  ---------- ---------- --R------- ---------- o--------- -------I-- ----------
pt. 3O        ---------  ---------- ---------- ---------- ---------- o--------- -----Y---- S---------
pt. 3Q        ---------  ---------- ---------- --R------- ---------- o--------- ---------- ----------
pt. 6A        ---------  ---------- ---------- ---------- ---------- o--------- ---------- -----I----
IFN Treatment
pt. B         ---------  ---------- ---------- ---------- ---------- o--------- -----Y---- ----------
pt. 1         ---------  ---------- ---------- ---------- ---------- o--------- ---------- ----------
pt. 179       ---------  ---------- ---------- ---------- ---------- o--------- ---------- S---------
1b amb.       --------*  -----*---- ---------- --*------- ---------- o--------* -----*--*- *--*-*----
Impt. A.A.    ---------  ---------- ---------- ----●●●●●● ●●●------- ----●●●●●● ●●●------- ---------- ----------
                                                   Motif I              Motif Ia                    Nucleic Acid
                                                                                                    Binding
```

```
                  270        280        290        300        310        320        330        340
Consensus     TGAPITYSTY GKFLADGGCS GGAYDIIICD ECHSTDSTTI LGIGTVLDQA ETAGARLVVL ATATPPGSVT VPHPNIEEVA
1b            --GS----o- ---------- ---------- ---------- ---------- ---------- ---------- --------IG
No Treatment
pt. 128       --------o- ---------- ---------- ---------- ---------- ---------- ---------- ----------
pt. 1A        ---S----o- ---------- ---------- ----I-A--- --V------- ---------- ---------- ----------
pt. 1G        --------o- ---------- ---------- -------S-- ---------- ---------- ---------- ---S------
pt. 1U        --------o- ---------- -------M-- ---------- ---------- ---------- ---------- ----------
pt. 2D        ---S----o- ---------- ---------- -------S-- ---------- ---------- ---------- ----------
pt. 2F        --------o- ---------- ---------- ---------- ---------- ---------- ---------- ----------
pt. 3N        ---S----o- ---------A ---------- ---------- ---------- ---------- ---------- ----------
pt. 3O        --------o- ---------- ---------- -------S-- ---------- ---------- ---------- ----------
pt. 3Q        ----V---o- ---------- ---------- -------S-- ---------- ---------- ---------- ----------
pt. 6A        ---S----o- ---------- ---------- -------A-- --V------- ---------- ---------- ----------
IFN Treatment
pt. B         --------o- ---------- ---------- -------S-- ---------- ---------- ---------- ----------
pt. 1         --------o- ---------- ---------- ---------- ---------- ---------- ---H------A- ----------
pt. 179       --------o- ---------- ---------- ---------- ---------- ---------- ---------- ----------
1b amb.       --***---o- ---------* -------*-- ----*-*-*- --*------- ---------- ---------- ---*----**
Impt. A.A.    ---●●●●●●● ●●●●●----- -----●●●●● ●●●●●●---- ---------- -----●●●●● ●●●●●●●●●- ----------
              Nucleic Acid Binding      Motif II                                Motif III
```

```
                  350        360        370        380        390        400        410        420
Consensus     LSTTGEIPFY GKAIPIETIK GGRHLIFCHS KKKCDELAAK LSGLGLNAVA YYRGLDVSVI PTSGDVVVVA TDALMTGFTG
1b            ---N------ -------A-- ---------o ---------- -T-------- ---------- -PI------- o---------
No Treatment
pt. 128       ---------- ---------- ---------o --------T- --S------- ---------- ---------- o---------
pt. 1A        ---------- -------A-- ---------o ---------- ---------- ---------- ---------- o---------
pt. 1G        ---------- -------A-- ---------o ---------- ---------- ---------- -V-------- o---------
pt. 1U        ---------- ---------- ---------o ---------- ---------- ---------- -A-------- o---------
pt. 2D        ---------- -------A-- ---------o ---------- ---------- ---------- ---------- o---------
Pt. 2F        ---------- ---------- ---------o ---------- -----S---- ---------- -S-------- o---------
pt. 3N        ---I------ -----L-V-- ---------o ---------- --S--I---- ---------- ---------- o---------
pt. 3O        ---------- ---------- ---------o ---------- -R---I---- ---------- ----A----- o---------
pt. 3Q        ---I------ -------V-- ---------o ---------- -----I---- ---------- ---------- o------Y--
pt. 6A        ---I------ ---------- ---------o ---------- -----F---- ---------- -S-------- o---------
IFN Treatment
pt. B         ---I------ ---------- ---------o ---------- -----I---- ---------- ---------- o---------
pt. 1         ---I------ ---------- ---------o ---------- ---------- ---------- ---------- o---------
pt. 179       ---------- -------A-- ---------o ---------- ---------- ---------- ---------- o---------
1b amb.       ---*------ -----*-*-- ---------o ---------* -**--*---- -*-------- -**------- o------*--
Impt. A.A.    ---------- ---------- -----●●●●● ●●●●------ ---------- ---------- -----●●●●● ●●●●●●●●●-
                                        Motif IVa                                      Motif V
```

TABLE 5B-continued

```
                    430        440        450        460        470        480        490        500
Consensus      DFDSVIDCNT CVTQTVDFSL DPTFTIETTT VPQDAVSRSQ RRGRTGRGRR GIYRFVTPGE RPSGMFDSSV LCECYDAGCA
1b             ---------- ---------- ---------- ---------- ---------S ---------- ---------- ----------
No Treatment
pt. 128        ---------- ---------- ---------- ---------- ---------- ------V-T- ---------- ----------
pt. 1A         ---------- ---------- ---------- ---------- ---------- -----A---- ---------- ----------
pt. 1G         ---------- ---------- ---------- ---------- ---------- -----M---- ---------- ----------
pt. 1U         ---------- ---------- ---------- ---------- ---------- -----M---- ---------- ----------
pt. 2D         ---------- ---------- ---------- ---------- ---------- ---------- ---------- ----------
Pt. 2F         ---------- ---------- ---------- ---------- ---------- ---------- ---------- ----------
pt. 3N         ---------- ---------- ---------- ---------- ---------- -----M---- ---------- ----------
pt. 3O         ---------- ---------- ---------- ---------- ---------- -----P---- --------R- ----------
pt. 3Q         ---------- ---------- ---------- ---------- ---------- -----G---- ---------- ----------
pt. 6A         ---------- ---------- ---------- ---------- ---------- -----S---- ---------- ----------
IFN Treatment
pt. B          ---------- ---------- ---------- ---------- ---------- ---------- ---------- ----------
pt. 1          ---------- ---------- ---------- ---------- ---------- -----A---- ---------- ----------
pt. 179        ---------- ---------- ---------- ---------- ---------- -----G---- ---------- ----------
1b amb.        ---------- ---------- ---------- ---------- ---------* -*---*--*- ---------- ----------
Impt. A.A.     ----●●●●●● ●●●●------ ---------- ---------- ---------● ●●●●●●●●●● ---------- ------●●●●
                   Gatekeeper                                             Motif VI                              Gatekeeper
```

```
                    510        520        530        540        550        560        570        580
Consensus      WYELTPAETS VRLRAYLNTP GLPVCQDHLE FWESVFTGLT HIDAHFLSQT KQAGDNFPYL VAYQATVCAR AQAPPPSWDQ
1b             ○--------- ---------- ---------- ---------- ---------- ---------- ---------- ----------
No Treatment
pt. 128        ○--------- ---------- ---------- ---------- ---------- ---------- T--------- ----------
pt. 1A         ○--------- ---------- ---------- ---------- ---------- ----H-Y--- T--------- ---------E
pt. 1G         ○--------- ---------- ---------- ---------- ---------- ---------- ---------- ----------
pt. 1U         ○--------- ---------- ---------- ---------- ---------- ---------- ---------- ----------
pt. 2D         ○--------- ---------- ---------- ---------- ---------- ---------- T--------- ----------
pt. 2F         ○--------- ---------- ---------- ---------- ---------- ----E----- ---------- ---------*
pt. 3N         ○--------- ---------- R--------- ---------- ---------- ---------- ---------- ----------
pt. 3O         ○--------- ---------- R--------- ---------- -V-------- ---------- ---------- ----------
pt. 3Q         ○--------- ---------- R--------- ---------S ---------- ---------- ---------- ----------
pt. 6A         ○--------- ---------- ---------- ---------- ---------- ----E----- ---------- ----------
IFN Treatment
pt. B          ○--------- ---------- ---------- ---------- ---------- ---------- ---------- ----------
pt. 1          ○--------- ---------- ---------- ---------- ---------- ---------- T--------- ----------
pt. 179        ○-------T- ---------- ---------- ---G------ ---------- ---------- ---------- ----------
1b amb.        ○-------*- ---------- *--------- ---*-----* -*-------- ----*-*--- *--------- ---------*
Impt. A.A.     ●●●●●----- ---------- ---------- ---------- ---------- ---------- ---------- ----------
               Gatekeeper
```

```
                              590        600        610        620        630
                Consensus   MWKCLIRLKP TLHGPTPLLY RLGAVQNEVT LTHPITKYIM ACMSADLEVV T
                1b          ---------- ---------- ---------I ---------- ---------- -
                No Treatment
                pt. 128     ---------- ---------- ---------- ---------- ---------- -
                pt. 1A      ---------- ---------- ---------- ---------- ---------- -
                pt. 1G      -----T---- ---------- ---------N ---------- ---------- -
                pt. 1U      ---------- ---------- ------DI-- ----V----- ---------- -
                pt. 2D      ---------- ---------- ---------I ---------- ---------- -
                pt. 2F      -----T---- ---------- ---------- ---------- ---------- -
                pt. 3N      ---------- ---------- ---------- -------L-- ---------- - pt. 3O      ---------- ---------- K-G------- ---------- T--------- -
                pt. 3Q      ---------- ---------- ---------- ----V----- T--------- -
                pt. 6A      ---------- ----S----- ---------- ---------- ---------- -
                IFN Treatment
                pt. B       -----T---- ---------- ---------- ----V----- T--------- -
                pt. 1       ---------- ---------- ---------I- ---------- T--------- -
                pt. 179     ---------- ---------- ---------- ---------- ---------- -
                1b amb.     -----*---- ----*----- *-*----*** ----*--*-- *--------- -
                Impt. A.A.  ---------- ---------- ---------- ---------- ---------- -
```

What is claimed is:

1. A set of primers comprising:
   (a) a primer of 4 to 30 nucleotides in length comprising the sequence of SEQ ID NO: 3; and
   (b) a primer of 4 to 30 nucleotides in length comprising the sequence of SEQ ID NO: 23, wherein each said primer is capable of annealing to the NS3 or NS4 gene of HCV or a portion of the NS3 or NS4 gene of HCV.

2. An isolated nucleic acid molecule of 4 to 30 nucleotides in length comprising the sequence of either SEQ ID NO: 3 or SEQ ID NO: 23, wherein the isolated nucleic acid molecule is capable of annealing to the NS3 or NS4 gene of HCV or a portion of the NS3 or NS4 gene of HCV.

3. The isolated nucleic acid molecule of claim 2 wherein the nucleotide sequence is identical to the sequence of SEQ ID NO: 3.

4. The isolated nucleic acid molecule of claim 2 wherein the nucleotide sequence is identical to sequence of SEQ ID NO: 23.

5. The isolated nucleic acid molecule of claim 2 wherein the isolated nucleic acid molecule comprising the sequence of SEQ ID NO: 3 is 17 to 30 nucleotides in length.

6. The isolated nucleic acid molecule of claim 2 wherein the isolated nucleic acid molecule comprising the sequence of SEQ ID NO: 23 is 17 to 30 nucleotides in length.

7. The set of primers according to claim 1 wherein primer (a) is identical to the sequence of SEQ ID NO: 3.

8. The set of primers according to claim 1 wherein primer (b) is identical to the sequence of SEQ ID NO: 23.

9. The set of primers according to claim 1 wherein primer (a) comprising the sequence of SEQ ID NO: 3 is 17 to 30 nucleotides in length.

10. The set of primers according to claim 1 wherein primer (b) comprising the sequence of SEQ ID NO: 23 is 17 to 30 nucleotides in length.

11. A kit for the detection of HCV comprising an isolated nucleic acid molecule of 4 to 30 nucleotides in length comprising the sequence of either SEQ ID NO: 3 or SEQ ID NO: 23, wherein the isolated nucleic acid molecule is capable of annealing to the NS3 or NS4 gene of HCV or a portion of the NS3 or NS4 gene of HCV.

* * * * *